(12) United States Patent
Collins et al.

(10) Patent No.: US 9,164,053 B2
(45) Date of Patent: Oct. 20, 2015

(54) ELECTRONIC DEVICE FOR MONITORING SINGLE MOLECULE DYNAMICS

(71) Applicant: THE REGENTS OF THE UNIVERSITY OF CALIFORNIA, Oakland, CA (US)

(72) Inventors: Philip G. Collins, Santa Ana, CA (US); Gregory A. Weiss, Irvine, CA (US); Yongki Choi, Irvine, CA (US); Issa S. Moody, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 147 days.

(21) Appl. No.: 13/626,760

(22) Filed: Sep. 25, 2012

(65) Prior Publication Data
US 2013/0078622 A1    Mar. 28, 2013

Related U.S. Application Data

(60) Provisional application No. 61/539,220, filed on Sep. 26, 2011.

(51) Int. Cl.
*B82Y 30/00* (2011.01)
*G01N 27/26* (2006.01)
*G01N 27/414* (2006.01)
*B82Y 15/00* (2011.01)

(52) U.S. Cl.
CPC ............ *G01N 27/26* (2013.01); *G01N 27/4146* (2013.01); *B82Y 15/00* (2013.01)

(58) Field of Classification Search
None
See application file for complete search history.

(56) References Cited

U.S. PATENT DOCUMENTS

| | | | |
|---|---|---|---|
| 7,318,908 B1 | 1/2008 | Dai | |
| 7,714,386 B2 | 5/2010 | Pesetski et al. | |
| 8,029,734 B2 | 10/2011 | Dai et al. | |
| 8,072,008 B2 | 12/2011 | Mukasa et al. | |
| 2003/0064366 A1* | 4/2003 | Hardin et al. | 435/6 |
| 2006/0065887 A1* | 3/2006 | Tiano et al. | 257/20 |
| 2006/0275371 A1* | 12/2006 | Dai et al. | 424/489 |
| 2007/0264634 A1* | 11/2007 | Bock et al. | 435/6 |
| 2007/0278111 A1* | 12/2007 | Boussaad et al. | 205/792 |
| 2010/0231242 A1* | 9/2010 | Gabriel et al. | 324/692 |

FOREIGN PATENT DOCUMENTS

WO    WO 2012/097074 A2    7/2012

OTHER PUBLICATIONS

Goldsmith et al, Nano Letters, vol. 8, pp. 189-194, published on the web Dec. 19, 2007.*

(Continued)

*Primary Examiner* — Robert T Crow
(74) *Attorney, Agent, or Firm* — Mintz Levin Cohn Ferris Glovsky and Popeo, P.C.

(57) ABSTRACT

A single molecule sensing device includes a first electrode, a second electrode and a single-walled carbon nanotube (SWNT) connected to the first and second electrodes. At least one linker molecule having first and second functional groups is functionalized with a sidewall of the SWNT, the at least one linker molecule having the first functional group non-covalently functionalized with a sidewall of the single-walled carbon nanotube. A single sensitizing molecule having at least one functional group is functionalized with the second functional group of the at least one linker molecule.

14 Claims, 22 Drawing Sheets

(56) References Cited

OTHER PUBLICATIONS

Artyukhin, Alexander B. et al., Layer-by-Layer Electrostatic Self-Assembly of Polyelectrolyte Nanoshells on Individual Carbon Nanotube Templates, Langmuir 2004, 20, 1442-1448.
Besteman, Koen et al., Enzyme-Coated Carbon Nanotubes as Single-Molecule Biosensors, Nano Letters, 2003, vol. 3, No. 6, 727-730.
Claridge, Shelley A. et al., Electrons, Photons, and Force: Quantitative Single-Molecule Measurements from Physics to Biology, ACSNano, www.acsnano.org., vol. 5, No. 2, 693-729 (2011).
Chen, Robert J. et al., Noncovalent Sidewall Functionalization of Single-Walled Carbon Nanotubes for Protein Immobilization, J. Am. Chem. Soc. 2001, 123, 3838-3839.
Goldsmith, Brett R. et al., Conductane-Controlled Point Functionalization of Single-Walled Carbon Nanotubes, Science 315, 77 (2007).
Gruner, G., Carbon Nanotube Transistors for Biosensing Applications, Anal Bioanal Chem (2006) 384: 322-335.
Ha, Taekjip, Single-Molecule Fluorescene Resonance Energy Transfer, Methods 25, 78-86 (2001).
Hirsch, Andreas et al., Functionalization of Carbon Nanotubes, Top Curr Chem (2005) 245: 193-237.
Huang, Shuo et al, Identifying Single Bases in a DNA Oligomer with Electron Tunnelling, Nature Nanotechnology, vol. 5, Dec. 2010, 868-873.
Karachevtsev, Victor A. et al., Noncovalent Interaction of Single-Walled Carbon Nanotubes with 1-Pyrenebutanoic Acid Succinimide Ester and Glucoseoxidase, J. Phys. Chem. C 2011, 115, 21072-21082.
Li, Jing et al., Carbon Nanotube Based Chemical Sensors for Space and Terrestial Applications, NASA Ames Research Center, Moffett Field, CA 94035 (7 pages).
Perrello, David J. et al., Analysis of Hopping Conduction in Semiconducting and Metallic Carbon Nanotube Devices, Journal of Applied Physics 105, 124309 (2009).
Star, Alexander et al., Electronic Detection of the Enzymatic Degradation of Starch, Organic Letters 2004, vol. 6, No. 13, 2089-2092.
Sorgenfrei, Sebastian et al., Label-free Single-molecule Detection of DNA-Hybridization Kinetics with a Carbon Nanotube Field-effect Transistor, Nature Nanotechnology, vol. 6, Feb. 2011, 126-132.
Sorgenfrei, Sebastian et al., Debye Screening in Single-Molecule Carbon Nanotube Field-Effect Sensors, Nano Lett. 2011, 11, 3739-3743.
Star, Alexander et al., Electronic Detection of Specific Protein Bing Using Nanotube FET Devices, Nano Letters 2003, vol. 3, No. 4, 459-463.
Tsutsui, Makusu et al., Single-molecule Sensing Electrode Embedded In-plane Nanopore, Scientific Reports, 1:46 DOI: 10. 1038/srep00046 (6 pages).
Zhao, Yan-Li et al., Pyrenecyclodextrin-Decorated Single-Walled Carbon Nanotube Field-Effect Transistors as Chemical Sensors, Adv. Mater. 2008, 20, 1910-1915.

* cited by examiner

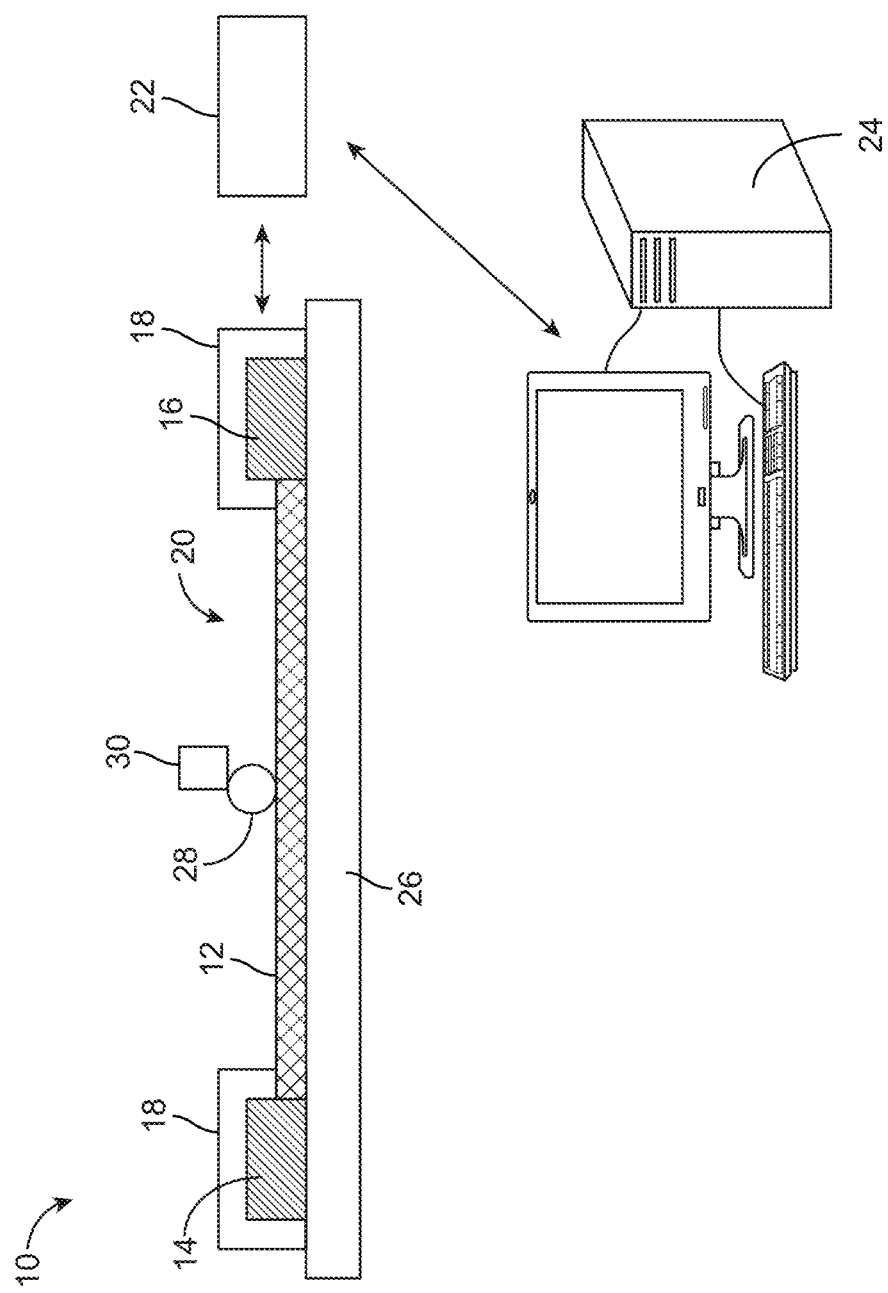

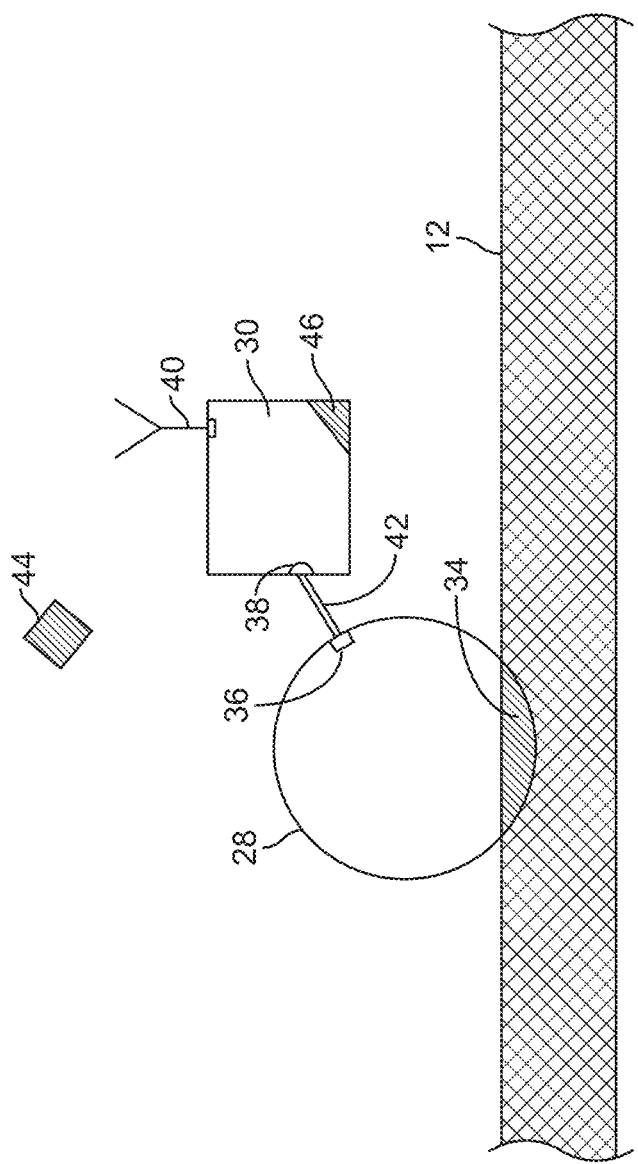

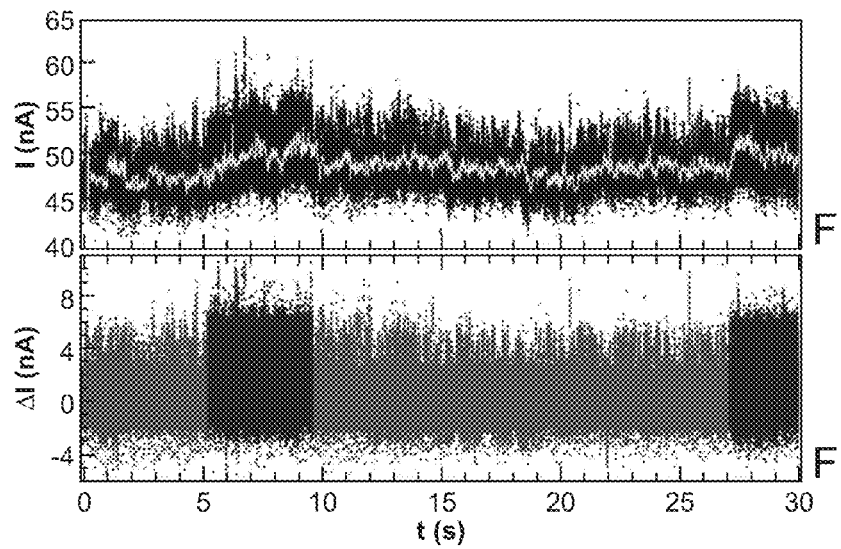
FIG. 2A
FIG. 2B
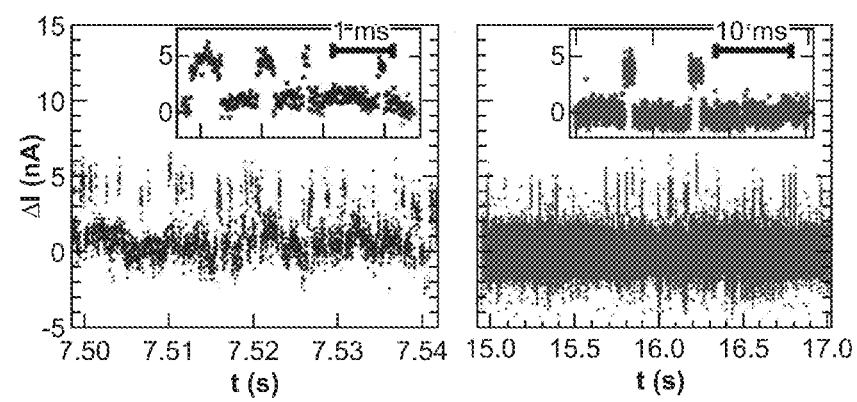
FIG. 2C        FIG. 2D

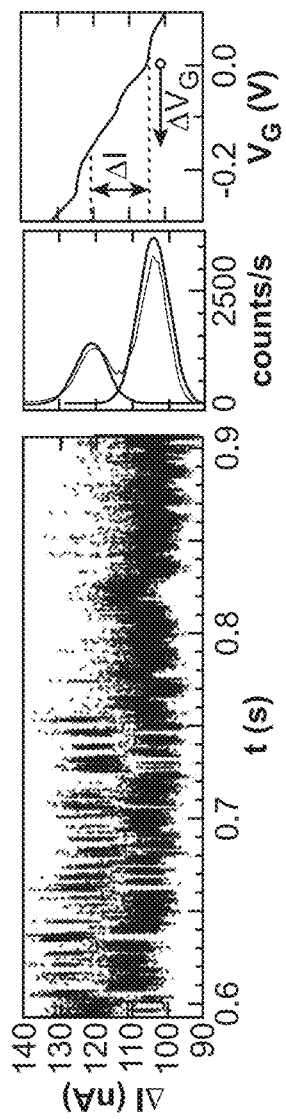
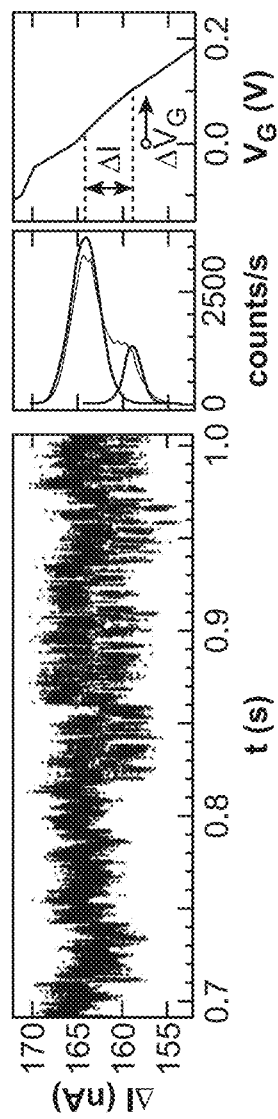
FIG. 12A
FIG. 12B

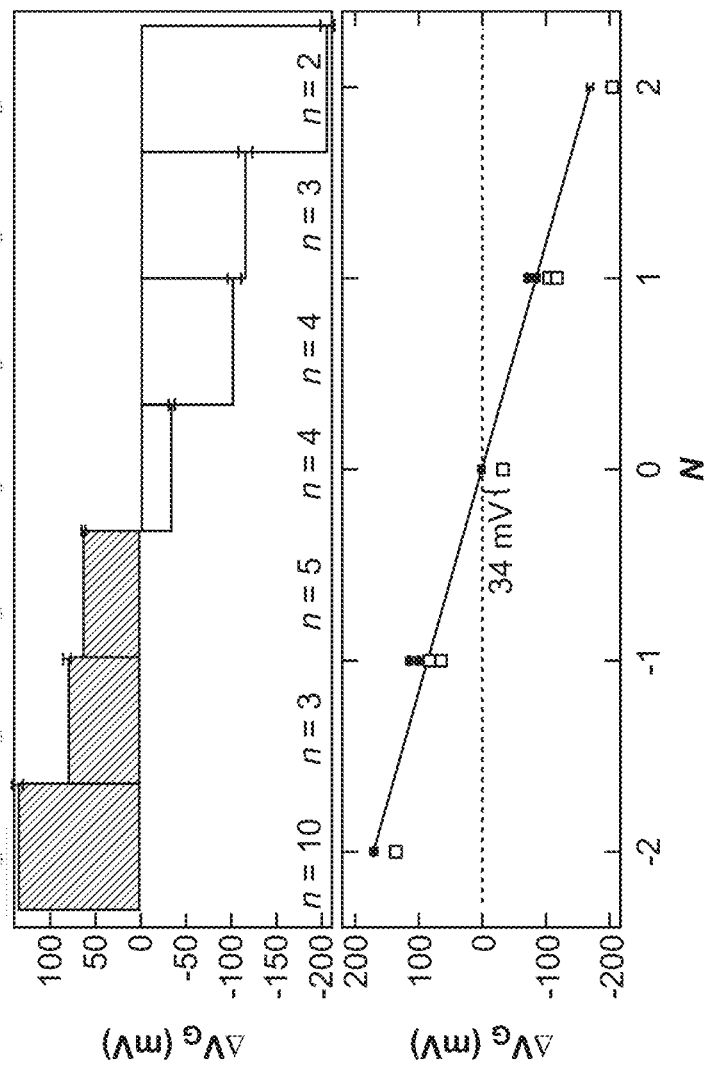

ELECTRONIC DEVICE FOR MONITORING SINGLE MOLECULE DYNAMICS

RELATED APPLICATION

This application claims priority to U.S. Provisional Patent Application No. 61/539,220, filed on Sep. 26, 2011, which is hereby incorporated by reference in its entirety. Priority is claimed pursuant to 35 U.S.C. §119.

STATEMENT REGARDING FEDERALLY SPONSORED RESEARCH OR DEVELOPMENT

This invention was made with Government support from the National Cancer Institute of the National Institutes of Health under Grant No. R01 CA133592-01; and the National Science foundation under Grants No. CHE-0802913, DMR-0801271, and ECCS-0802077. The Government has certain rights in this invention.

FIELD OF THE INVENTION

The field of the invention generally relates to electronic sensors, and more specifically to the field of sensors comprising single-walled carbon nanotubes.

BACKGROUND

A biosensor is an analytical device that incorporates a biological recognition element in direct spatial contact with a transduction element. That integration ensures the rapid and convenient conversion of biological events to detectable signals. Among diverse electrical biosensing architectures, devices based on field-effect transistors (FETs) have attracted great attention because they are a type of biosensor that can directly translate interactions between target molecules (e.g., biological molecules) and the transistor surface into readable electrical signals. In a standard field effect transistor, current flows along a conducting path (the channel) that is connected to two electrodes, (the source and the drain). The channel conductance between the source and the drain is switched on and off by a third (gate) electrode that is capacitively coupled through a thin dielectric layer. Field-effect transistors detect target chemicals and measure chemical concentrations for a wide range of commercial applications including, for example, industrial process control, leak detection, effluent monitoring, and medical diagnostics.

A problem with field-effect transistors is their limit of sensitivity. Field-effect transistors are not able to accomplish single molecule detection, i.e., these transistors are not able to detect at the level of one single molecule. Additionally, these transistors are not able to monitor the dynamics of a single molecule reaction. The sensitivity limitation of field-effect transistors prevents their use as detectors in important biochemical assays, such as detectors in a single molecule sequencing reaction.

Improving upon sensitivity has been explored in the past using devices based on single-walled carbon nanotubes (SWNTs). See A. Star et al., Nano. Lett. 3, 459 (2003); A. Star et al., Org. Lett. 6, 2089 (2004); K. Besterman et al., Nano. Lett. 3, 727 (2003); G. Gruner, Anal. Biooanal. Chem. 384, 322 (2005); R. Chen et al. Proc. Natl. Acad. Sci. U.S.A. 100, 4984 (2003). The motivation for using SWNTs in sensor FETs is that SWNTs are extremely small conductors, typically only 1 nanometer in diameter.

Past research has coated SWNT sensor FETs with chemoselective polymers, metal and metal oxide nanoparticles, and biomolecules like proteins and antibodies. These sensitizing molecules or sensitizing agents direct the innate sensitivity of the SWNT towards a particular chemical target. Past work has exclusively used coatings of sensitizing agents in which numerous molecules were attached to the SWNT. See K. Besterman et al., Nano. Lett. 3, 727 (2003); R. Chen et al. Proc. Natl. Acad. Sci. U.S.A. 100, 4984 (2003). Prior work, however, has lacked any method to controllably attach single sensitizing molecules to the SWNT, and the use of multiple sensitizing molecules typically resulted in a mixture of true signal and ensemble properties. This has complicated the analysis of any data acquired from the sensor FET, and precluded the application of probing a single molecule's dynamics.

The state of the art in improving this embodiment to single molecule sensitivity has used a special technique for creating one single covalent defect on the SWNT. See Goldsmith et al. Science 315, 77 (2007). Once the SWNT contains a single defect, a variety of attachment chemistries can be chosen which link to the reactive defect site selectively, without coating the rest of the SWNT with additional sensitizing molecules. This method of fabrication previously relied on electrochemical oxidation of the SWNT, creating a defect site on the wall of the SWNT constituting a functional group, followed by covalent functionalization of the sensitizing molecule to the defect site functional group. See Goldsmith et al, Nano Letters 8, 189 (2008); Coroneus et al. ChemPhysChem 9, 1053 (2008); Sorgenfrei et al., Nat. Nano. 6, 126 (2011). This method provides a single molecule device that is sensitive to dynamic fluctuations. The SWNT defect also invariably results in a drop in the conductivity of the SWNT and an increase in device noise, both as a result of the necessary disruption of the SWNT's $sp^2$ conjugation and aromaticity. Reports of this technique indicate that when electrochemical oxidation is terminated to result in a 90% reduction in conductivity, 88% of the devices remain conductive, but of those only 19% of devices yield functional devices with single sensitizing molecules attached. When electrochemical oxidation is terminated at greater than a 99% reduction in conductivity, only 18% of the devices remain conductive, and of those only 28% yield functional single sensitizing molecule devices. Coroneus et al. established process controls that achieved higher yields approaching 40%. Nevertheless, devices fabricated using this method usually display great chemical variability near the defect site, including broken carbon-carbon bonds which may be tautomerized or protonated, creating high variability among the electronic characteristics of different devices. Furthermore, devices of this type can only be fabricated serially, one device at a time. No methods exist for producing multiple, single-molecule devices in parallel.

SWNTs can also be tailored with sensitizing molecules by non-covalent means. In a non-covalent scheme, sensitizing molecules are weakly bound to SWNTs, thus preserving the $sp^2$ SWNT structure and resulting in more consistent electronic characteristics. See Chen et al, J. Am. Chem. Soc. 123, 3838 (2001). However, such methods do not reveal a method to reliably bind a single sensitizing molecule non-covalently to a SWNT, nor does the prior art demonstrate any device that utilizes a single, non-covalently bound sensitizing molecule.

Consequently, there remains a need for electronic devices that can achieve single molecule dynamic sensing, especially if those devices can be fabricated in greater yields, with chemical functionality, and with more consistent electronic characteristics. Potential applications of a robust system which is capable of the long-term probing and detecting of the dynamics of single molecules could include environmental detection, medical diagnostic tools, biomolecule sequencing such as DNA or RNA sequencing, and other fields of interest, such as security or defense.

SUMMARY

The invention generally provides an electronic device that is sensitive enough to detect at the single molecule level. Aspects of the invention are accomplished using an electrically-conducting channel that has a single sensitizing molecule attached thereto. Accordingly, devices of the invention monitor the dynamics of a single molecule reaction, and can be used in important single molecule biochemical assays, such as detectors in a single molecule sequencing reaction.

Any type of conduction channel that is generally found in field effect transistors can be used with the invention. Exemplary conduction channels are formed from metals, metal oxides, semiconductors, or nanometer-scale conductors such as nanowires, graphene, or single-walled carbon nanotubes (SWNTs). In one embodiment, the conduction channel is a single SWNT.

As a class of materials, SWNTs are semiconductors with electronic bandgaps that can vary from 1 electron volt to effectively zero. This variation leads to the classification of carbon SWNTs as metallic or semi-metallic, and others as semiconducting. With the aid of connecting electrodes, electrostatic gates, and other control circuitry, semiconducting SWNTs can be configured as sensor FETs, as RF amplifiers, or as low-temperature single electron transistors. The device and method does not preclude such additions, because the preferred embodiment is composed of only a two-terminal, SWNT conductor. SWNTs are preferred as conduction channels because single molecule sensing devices can be fabricated from SWNT wires of any type, with or without gate electrodes, and on glass, plastic, or silicon substrates. The single molecule sensing device described here can be one component within a FET or any number of more complex electronic or opto-electronic devices and circuitry.

One aspect of the invention is the reliable achievement of only one active sensitizing molecule in each device. In general, sensitizing molecules will coat a SWNT with a mean spacing that is determined by the concentration and incubation period used in preparation. Once that mean spacing has been empirically determined for a particular set of conditions, the SWNT conductor can be defined by lithography to have an equal length. In practice, this length is typically 1 to 100 nm when sensitizing molecules directly attach to the SWNT conductor, a range that is a difficult to control using optical lithography.

In the preferred embodiment, linker molecules serve as an attachment intermediary that improves the control over the mean separation of sensitizing molecules. Any method known in the art may be used to attached the single sensitizing molecule to the conductor. In certain embodiment, a linker molecule is used to attach the single sensitizing molecule. In particular embodiments, the linker molecule includes at least a first and a second functional group. Generally, the first functional group interacts with the conduction channel (e.g., the single-walled carbon nanotube) and the second functional group interacts with the sensitizing molecule. Exemplary first functional groups include a pyrene, a benzene, a cyclohexane, and 2,3-dichloro-5,6-dicyano-1,4-benzoquinone. An exemplary second functional group is maleimide. In certain embodiments in which the conduction channel is a SWNT, the linker molecule interacts with a sidewall of the SWNT through pi-pi stacking.

Using linkers, the length between sensitizing molecules can be dramatically increased up to 1 micrometer or more. With sensitizing molecules spaced 1 micrometer apart, it becomes possible to use standard lithographic masking techniques to define wafers full of conductors, each approximately 1 micrometer in length. Alternately, given a desired device pitch as set by the mask design, the concentration of sensitizing molecules and duration of incubation can be varied to achieve the same result of one molecule per device. The single molecule sensing devices can be produced in at least 8 out of 10 fabrication attempts, all without disrupting the $sp^2$ character of a SWNT conductor.

Any sensitizing molecules known in the art can be used with devices of the invention, and the sensitizing molecule chosen will depend on the molecule to be detected or the reaction to be monitored. Exemplary sensitizing molecules include an enzyme, a protein, a nucleic acid, a ribozyme, an aptamer, and a polysaccharide. In certain embodiments, the enzyme is a lysozyme, a protein kinase A, or a DNA Polymerase I.

In other aspects, more than one sensitizing molecule may be necessary in each device to achieve single molecule dynamic sensing. For example, at a desired operating temperature or pH, a particular type of sensitizing molecule might only have a 25% probability of being chemically active. Under these conditions, it is appropriate to attach additional sensitizing molecules (e.g., four) to each conductor in order to produce a device in which one is likely to be active. This higher density of attachments is readily achieved using the scheme described above, either by increasing the length of the devices to an appropriate multiple of the mean separation distance between molecules, or else by decreasing the same separation by modifying the attachment conditions.

In one embodiment, the single molecule sensing device includes multiple conductors in parallel (e.g., SWNT conductors). A single active sensitizing molecule is attached to one of the conductors, and it contribute a dynamic electronic signal that is separable from the parallel but static conductance of the unmodified conductors. This embodiment provides additional flexibility in the design of the conductor synthesis or placement, and in the successful fabrication of single molecule sensing devices using sensitizing molecules that have very low attachment probabilities.

In one particular embodiment, multiple single molecule sensing devices are fabricated in parallel using the same type of sensitizing molecule, with one sensitizing molecule attached per device. In another embodiment, multiple conductors are prepared and then exposed to different sensitizing molecules, in order to achieve multiple single molecule sensing devices that are sensitized towards differing targets. In another embodiment, the single molecule sensing device responds to multiple targets through a sensitizing molecule with a range of specificities.

In one embodiment, a single molecule sensing device includes a first electrode, and a second electrode. A single-walled carbon nanotube is connected, respectively, to the first electrode and the second electrode. The device includes at least one linker molecule having first and second functional groups, the at least one linker molecule having the first functional group non-covalently functionalized with a sidewall of the single-walled carbon nanotube. A single sensitizing molecule having at least one functional group, said at least one functional group of the single sensitizing molecule being functionalized with the second functional group of the at least one linker molecule.

In another embodiment, a method for making a single molecule sensing device includes forming at least one single-walled carbon nanotube on a substrate that is connected to a first electrode and a second electrode; non-covalently functionalizing the single-walled carbon nanotube sidewall of the device with at least one functional group of at least one linker molecule containing a plurality of functional groups; and functionalizing at least one of the functional groups of the at least one linker molecule with one or more functional groups of a single sensitizing molecule.

In another embodiment, a method of using a single molecule sensing device having a single-walled carbon nanotube (SWNT) is disclosed. The SWNT is disposed on a substrate and connected to a first electrode and a second electrode, the sensing device having a single sensitizing molecule secured to the SWNT using a linker molecule non-covalently functionalized with the SWNT. Voltage is applied across the SWNT. The sensitizing molecule is exposed to a chemical environment. Fluctuations in the current flowing through the SWNT are monitored.

In another embodiment, methods for sequencing a nucleic acid using a single molecule sensing device is disclosed. The sensing device includes a conductive channel. The conductive channel may include a single-walled carbon nanotube (SWNT) on a substrate connected to a first electrode and a second electrode. The sensing device has a single sensitizing enzyme secured to the channel using a linker molecule non-covalently functionalized with the channel (e.g., SWNT). The method includes exposing the device to at least one type of nucleotide; applying a voltage potential across the channel; monitoring fluctuations in the current flowing through the SWNT; and identifying the nucleotides incorporated into a nucleic acid template by the enzyme based at least in part on the monitored fluctuations in current. The enzyme may be a polymerase or a reverse transcriptase. The nucleotide may be a nucleotide analog. In certain embodiments, the device is exposed to more than one type of nucleotide at a single time.

The sensing device may also be used to determine processing kinetics of a protein or enzyme. Still another application of the sensing device is to determine the effects of a genetic mutation. Devices using sensitizing molecules or targets with genetic mutations can be compared to the performance obtained from similar devices with sensitizing molecules or targets that do not have the mutation. In still another application, the sensing devices can be used to measure the effects of drugs or other small molecules on a protein, either to make it active or inactive.

Method of fabricating devices of the invention may involve a biochemical conjugation protocol followed by controlled rinsing. Such a process results in devices of the invention having one sensitizing molecule and no nonspecific binding of interfering molecules. In certain embodiments, the sensitizing molecule is directly attached to the conductor through a non-covalent interaction. In other embodiments the sensitizing molecule is attached to an intermediate linker molecule having at least two functional groups, one designed for the non-covalent attachment and the other for versatile bio-conjugation to a sensitizing molecule. One scheme of using an intermediate linker provides a chemically versatile platform for building devices of the invention from a wide class of sensitizing molecules.

In another embodiment, a method for making a single molecule sensing device includes forming at least one single-walled carbon nanotube on a substrate that is connected to a first electrode and a second electrode, non-covalently functionalizing the single-walled carbon nanotube sidewall of the device with at least one functional group of at least one linker molecule containing a plurality of functional groups; and functionalizing at least one of the functional groups of the at least one linker molecule with one or more functional groups of a single sensitizing molecule.

BRIEF DESCRIPTION OF THE DRAWINGS

FIG. 1A illustrates a schematic representation of a single molecule sensing device according to one preferred aspect of the invention.

FIG. 1C schematically illustrates a linker molecule along with a sensitizing molecule associated with a carbon SWNT.

FIG. 2A illustrates an extended sequence of current fluctuation over 30 seconds, with the mean value highlighted using the setup of Example 2.

FIG. 2B shows the instantaneous deviations from the mean current, coded into two different types of behaviors according to the two types of motion of the lysozyme protein being probed.

FIG. 2C shows in detail the "fast switching" fluctuations of lysozyme protein doing nonproductive binding.

FIG. 2D shows in detail the "slow switching" fluctuations of lysozyme protein doing catalytic processing.

FIG. 12A shows the response and response histogram from a lysozyme device fabricated using a lysozyme variant (R119A) having a single positive charge in the conductivity-modulation component.

FIG. 12B shows the response and response histogram from a lysozyme device fabricated using a lysozyme variant (K83A/R119E) having a single negative charge in the conductivity-modulating component.

FIG. 13A illustrate seven lysozyme variants that differ only in the net charge of N electrons present on their conductivity-modulating components.

FIG. 13B shows the effective electrostatic voltage generated at the SWNT by the conductivity-modulating component of each lysozyme variant.

FIG. 13C shows that the electrostatic effect of the conductivity-modulating component is proportional to the net charge of N electrons.

DETAILED DESCRIPTION OF THE ILLUSTRATED EMBODIMENTS

Figure 1B:
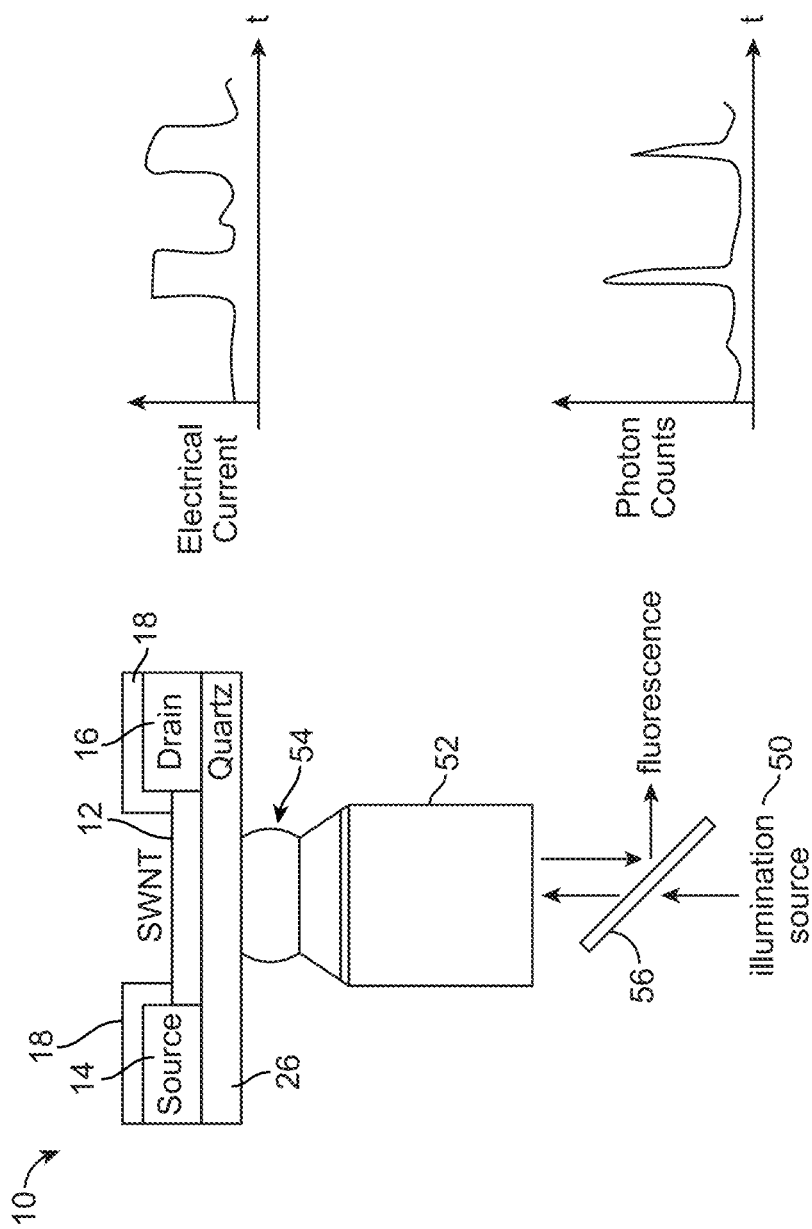
FIG. 1B illustrates another embodiment of a single molecule sensing device according to an alternative embodiment.

FIG. 1A illustrates a schematic representation of a single molecule sensing device 10 according to one preferred aspect of the invention. The device 10 includes a single-walled carbon nanotube (SWNT) 12 that is interposed between a first electrode 14 and a second electrode 16. While FIG. 1A illustrates a single SWNT 12, in alternative embodiments, there may be a plurality of SWNTs 12 located between the first electrode 14 and the second electrode 16. SWNTs are well known in the art and the specific design or method of manufacture of the SWNT can comprise any design or method of manufacture for SWNT suitable for use in the present invention. The first electrode 14 may include a source electrode while the second electrode 16 may include a drain electrode.

In one embodiment, the single molecule sensing device 10 may take the form of a transistor, namely, a field effect transistor (FET) with the attached biomolecules serving as a "gate" to an electrical circuit. In this embodiment, a single sensitizing molecule services a single molecule gate for the device. The transistor embodiment may include a two or three terminal transistor. The conduction channel may also be formed from metals, metal oxides, semiconductors, or nanometer-scale conductors such as nanowires, grapheme, or single-walled carbon nanotubes (SWNTs). In one embodiment, the conduction channel is a single SWNT.

Generally, the length of the SWNT 12 may vary from about 0.1 to about 10 micrometers. The particular length of the SWNT 12 is chosen such that statistically, a majority of the devices 10 that are manufactured have only a single sensitizing molecule associated with the SWNT 12. Even more preferably, the length of the SWNT 12 that is exposed to the external chemical environment is chosen such that more than 75% of the devices 10 that are manufactured include only a single sensitizing molecule associated with the SWNT 12. In some instances, this distance is the distance between the first electrode 14 and the second electrode 16.

Still referring to FIG. 1A, the first electrode 14 and the second electrode 16 may be optionally covered with a cover 18. The cover 18 may include a window 20, recess, slot, or other open segment that provides access from the external environment to the SWNT 12. In this regard, the SWNT 12 can be exposed to a chemical environment. For example, an exposed window 20 can be defined in the cover 18 during the manufacturing process. The protective covering ensures that the majority of the surface including the first and second electrodes 14, 16 is protected from the environment. Moreover, in a preferred embodiment, the length of the window 20 is tailored to achieve the correct device length. The length of the window 20 can be varied to achieve the desired active region on the SWNT 12. For example, the first and second electrodes 14, 16 may be connected to the SWNT 12 and separated by a distance of 2 µm. The window 20, however, can be made smaller than the inter-electrode distance. The exposed window 20 within the protective covering exposes the SWNT 12 and the attached sensitizing molecule to the chemical environment. The protective cover 18 can be any electrically-insulating film composed of one or more layers. Preferable film materials include polymers, aluminum oxide, halfnium oxide, silicon dioxide, or silicon nitride. The window 20 is defined within the protective covering using lithographic techniques. Lithographic techniques are well known in the art and comprise using any acceptable combination of optical exposure, electron beam methods, and positive or negative resists.

In a more preferred embodiment, device fabrication comprises coating devices in a protective covering of positive electron beam resist such as polymethyl methacrylate (PMMA); writing lithographic patterns with an electron beam; and then developing the written areas to expose an active SWNT channel 0.5 to 1.0 μm in length. In another embodiment, device fabrication comprises coating devices in a protective covering of aluminum oxide; coating devices further in a film of optical photoresist; exposing the desired windows to light; developing the written areas to expose narrow windows of the aluminum oxide; etching the aluminum oxide to further expose the underlying SWNT channels 0.5 to 1.0 μm in length. Combinations of two or more layers of materials in the protective coating provide coatings having different chemical properties.

Still referring to FIG. 1A, the device 10 is coupled to electronic circuitry 22. The electronic circuitry is used to both apply a voltage bias (e.g., 50-100 mV) between the first electrode 14 and the second electrode 16 and is also configured to measure the current flow across the SWNT 12 as a function of time. Electronic circuitry 22 may be coupled to a computer 24 having one or more processors therein that is used to control the application of voltage and current through the device 10 as well as acquire, store, and analyze data generated by the device 10. During operation of the device 10, a voltage (e.g., constant DC voltage or combination of AC and DC voltages) is applied between the first electrode 14 and the second electrode 16. The current then passing through the SWNT 12 is measured using electronic circuitry 22 which may include a current meter with one or more amplifiers.

The first electrode 14, second electrode 16, and the SWNT 12 may be disposed atop a substrate 26. The substrate 26 may include any number of substrate materials such as glass, plastic, or silicon. One alternative embodiment of the invention involves fabrication of the device on an optically transparent substrate such as glass or quartz. Unlike sensor FETs and much of the prior art related to sensing, the device 10 does not require a gate electrode or a conductive supporting substrate. Consequently, the device 10 can be fabricated on a wide range of surfaces including transparent ones. Quartz is preferred for the CVD fabrication process described above because it is compatible with high temperatures. Glass wafers can also be used if the SWNTs 12 are synthesized and deposited onto the substrate by other means, such as spin coating from solution, or if the devices are fabricated on wafers and then transferred to the glass for support. In any case, the use of quartz, glass, sapphire, or other transparent substrate enables optical monitoring of the device. Monitoring the fluorescence signal from tethered molecules is well known in the art, and it is best accomplished through a transparent substrate. A device 10 formed on a quartz substrate allows independent monitoring of molecule dynamics using the electrical techniques described herein and by optical techniques including single molecule fluorescence and smFRET.

One alternative embodiment of the invention is to acquire electrical and optical signals from the same single molecule, either at different times or simultaneously. This embodiment is illustrated in FIG. 1B. A single molecule sensing device 10 located on a transparent substrate 26 (e.g., quartz) provides a unique opportunity not found in the prior art to complement smFRET with an independent single molecule technique. In this embodiment, the SWNT 12 is illuminated through the transparent substrate 26 using an illumination source 50. Fluorescent light that is emitted can be collected using an objective lens 52 that uses oil or water 54 to contact the transparent substrate 26. Fluorescent light can be directed to a photon counter using, for example, a beam splitter 56. FIG. 1B also illustrates the dual electrical and photon signals.

Such dual-mode monitoring can calibrate the measurements made by one approach, such as the electronic monitoring with turnover measurements of fluorescence made at the ensemble level. Simultaneous interrogation of one molecule by two independent means provides the opportunity to study two different portions of the same molecule, for example to compare a portion that moves, a portion that accepts the transfer of charge, a portion that contains a catalytic site, or a portion that absorbs or emits photons. Synchronous monitoring of two such portions can determine the relative timing and causality of two events, such as the movement of the active site correlated with the conformational changes of a regulatory site. Furthermore, the transparent substrate allows light-induced activation of a catalytic site functionality or a light driven charge-transfer for examination of the resultant conformational change. The SWNT 12 may, in one embodiment, be integrated within a flow cell or the like such that a fluid can flow over the SWNT 12 for measurements. Alternatively, fluids may be selectively deposited on top of the device 10.

Still referring to FIG. 1A, the device 10 includes at least one linker molecule 28 containing one or more functional groups non-covalently attached to the external sidewall of a SWNT 12. Preferable functional groups include pyrene, benzene, cyclohexane, and 2,3-dichloro-5,6-dicyano-1,4-benzoquinone. Functional groups which non-covalently attach to the external sidewall of a SWNT 12 are well known in the art and the specific design for this functional group can comprise any design suitable for use in the present invention. Furthermore, the linker molecule(s) 28 contains one or more functional groups functionalized with another functional group which is or has been attached to the sensitizing molecule 30 in such a way as to maintain some or all of the functionality of the sensitizing molecule 30. Preferable pairs of functional groups include an azide and an alkyne, a NHS ester and an amine, a thiol and an alkyne, and a thiol and a maleimide. Functional groups which functionalize with other functional groups are well known in the art and the specific design for this functional group can comprise any design suitable for use in the present invention.

As illustrated in FIG. 1A, the device 10 includes a single sensitizing molecule 30 containing one or more functional groups functionalized with one or more functional group of one of the linker molecule 28 in such a way as to retain the functionality of the sensitizing molecule 30. Sensitizing molecules 30 of the present invention include any molecule. Preferable sensitizing molecules 30 include molecules that are chemically specific in their interactions with other molecules. More preferably, sensitizing molecules 30 may include polymers, proteins, DNA, RNA, ribozyme and/or aptamer, polysaccharide, or other biomolecule. Sensitizing molecules 30 are well known in the art and can comprise any sensitizing molecule suitable for use in the present invention.

FIG. 1C schematically illustrates one preferred embodiment of the device 10. As seen in FIG. 1C, the linker molecule 28 includes a first functional group 34 that adheres non-covalently to the wall of the SWNT 12 and a second functional group 36 that is designed to attach to the sensitizing molecule 30. The use of the linker molecule 28 avoids the difficulty of designing an effective, direct attachment between the sensitizing molecule 30 and the SWNT 12. In this embodiment, the linker molecule 28 and the sensitizing molecule 30 are effectively a single entity. In practice, achieving and controlling the desired surface density often requires that the linker molecule(s) 28 and sensitizing molecule 30 be prepared as two separate solutions, with the final linkage between them performed in place on the SWNT 12. As seen in FIG. 1C, the sensitizing molecule 30 includes a first functional group 38 and a second functional group 40 which may include a target-selective functional group. The first functional group 38 of the sensitizing molecule 30 binds to the second functional group 36 of the linker molecule 28. The binding can be any chemical interaction known in the art, for example, covalent or non-covalent binding. In certain embodiments, the binding is through a covalent bond 42. The second functional group 40 is designed to bind to a target molecule 44 or multiple target molecules 44 by any binding interaction. The sensitizing molecule 30 also includes a conductivity-modulating component 46 that is ideally located near the site of the SWNT attachment. The conductivity-modulating component 46 need not be in close proximity to the second functional group 40 but the two should communicate through mechanical, allosteric or electronic means, so that interactions of the sensitizing molecule 30 with the chemical target 44 induce dynamic changes in the conductivity-modulating component 46 of the same sensitizing molecule 30 to affect electronic changes in the SWNT 12.

Figure 1D:
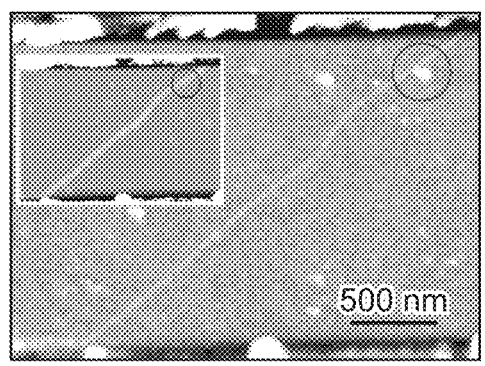
FIG. 1D illustrates an atomic force microscope tomography image of a device with the linker molecule being pyrene maleimide and the sensitizing molecule being lysozyme.
Figure 1E:
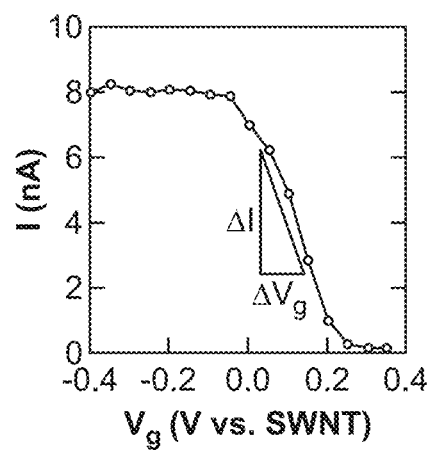
FIG. 1E illustrates the typical electrical characteristics of a completed device measured with aqueous electrolyte in direct contact with the sidewall of a semiconducting SWNT.
Figure 1F:
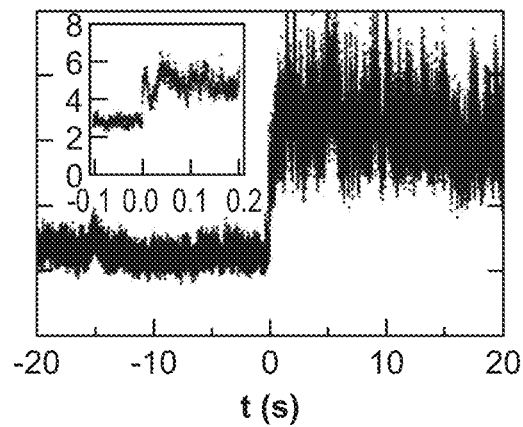
FIG. 1F illustrates the intrinsic electronic fluctuations of the device (t<0) and the enhanced fluctuations when probing molecular interactions (t>0).

FIG. 1D illustrates an atomic force microscope topography image of a device with the linker molecule being pyrene maleimide and the sensitizing molecule being lysozyme. The pyrene functional group non-covalently attaches to a SWNT surface through pi-pi stacking. A single sensitizing molecule is seen being associated with the SWNT. FIG. 1E illustrates the typical electrical characteristics of a completed device measured with aqueous electrolyte in direct contact with the sidewall of a semiconducting SWNT. The current I depends on the electrolyte bias $V_g$. FIG. 1F illustrates the intrinsic electronic fluctuations of the device (t<0) and the enhanced fluctuations when probing molecular interactions (t>0). The inset expands the time access near t=0. At time t=0 peptidoglycan substrate (25 µg/ml) was added to the solution.

In one alternative embodiment, all three components are combined in a single sensitizing molecule 30. For example, one amino acid of a protein might be an effective site for binding to a SWNT 12, another amino acid might have a net surface charge that can modulate the SWNT conductivity 46, and a third amino acid might serve as a recognition or binding site 44 for the protein's binding partner, the target molecule 44 to be detected. Alternately, a covalent or non-covalent complex can be designed and synthesized to bring all three components together as a single sensitizing agent.

In an alternate embodiment of the invention, the different functional components of the sensitizing molecule 30 are split among two or more molecules, all of which are covalently or non-covalently assembled on the SWNT conductor. In this alternative embodiment, the conductivity-modulation component can be a molecule that attaches to one functional group of a linker molecule 28, and the target-selective chemical component can be a second molecule that attaches to a different functional group of the same linker. Alternately, the target-selective chemical component can have a functional group that binds directly to the molecule that contains the conductivity-modulating component. This binding can be through a covalent bond or through non-covalent recognition or docking common to many biomolecules. In every case, some form of mechanical, steric or electrical communication will be achieved between the components, so that the dynamics of the target-specific chemical component result in changes to the conductivity-modulating component of the whole sensitizing complex.

An additional embodiment of the single molecule sensing device 10 includes a conductor having one or more SWNTs 12; one or more linker molecules 28 containing two or more functional groups, of which one or more is non-covalently bound to the surface of a SWNT 12; and a single sensitizing molecule 30 which contains at least one functional group which is functionalized to at least one functional group of a linker molecule 28.

A further embodiment includes a single molecule sensing device 10 wherein the linker molecule 28 contains a carboxylate group and the sensitizing molecule 30 contains an amine. The carboxylate functional group of the linker molecule 28 can be activated as a reactive ester and amidated using techniques that are well known in the art. The reactive ester can then be covalently coupled to an amine group of the sensitizing molecule 30 to form a stable amide bond in a way which is well known in the art.

A further embodiment of this invention includes a single molecule sensing device 10 wherein the linker molecule 28 is pyrene maleimide and the sensitizing molecule 30 contains a reactive thiol group. The maleimide functional group of the linker molecule 28 covalently couples with the thiol group of the sensitizing molecule 30 to form a stable thioester bond in a way which is well known in the art.

A further embodiment includes a non-covalent single molecule sensing device 10 wherein the linker molecule 28 is pyrene maleimide and the sensitizing molecule 30 is a protein. Further embodiments include those in which the protein is an enzyme. Further embodiments include those in which the enzyme is a cysteine variant of lysozyme, which has a single cysteine substituted for a surface residue to provide the reactive thiol for bio-conjugation. Lysozyme provides a good model protein to elucidate detailed enzyme dynamics and conformational motions from single molecule observations. In still other alternative embodiments, the enzyme is protein kinase A or DNA polymerase or a Reverse Transcriptase. Similar yields of single molecule sensing devices utilizing each of these enzymes have been achieved by tailoring the solution pH, soak duration, and rinse conditions used during attachment of the enzyme.

In alternative embodiments, the sensitizing molecule 30 is a nucleic acid (e.g., DNA, RNA), ribozyme, aptamer, polysaccharide, or other biomolecule. Any sensitizing molecule 30 which undergoes an alteration in conformational dynamics upon binding of or acting upon a substrate or ligand is suitable for use in the present invention. Further alternative embodiments comprise those wherein the linker molecule 28 comprises a linker molecule 28 containing at least one functional group which is known in the art to non-covalently functionalize to the surface of a SWNT 12 and at least one functional group being a functional group which is known in the art to form bonds with another functional group.

An additional embodiment of the invention is the use of a DNA or RNA polymerase or a Reverse Transcriptase as the single sensitizing molecule 30 non-covalently attached to the SWNT to allow the non-optical sequencing of DNA, cDNA or RNA molecules. Enzymes which catalyze the template-dependent incorporation of dNTPs are known to undergo well characterized conformational changes that can be used to monitor the nucleotide specific incorporation of natural or analog dNTPs or NTPs in accordance with the methods and devices described herein and thus provide the sequence of the template molecule. This label-free sequencing method has advantages over the currently practiced non-optical sequencing methods insofar as it allows the discrimination of a nucleotide specific incorporation event from a homogeneous mixture of four natural or analog dNTPs or NTPs, though the present invention is compatible with the practice of flowing individual dNTPs or analog dNTPs or NTPs in a serial and cyclic fashion for the purposes of sequence determination. The use of a Reverse Transcriptase as the non-covalently bound sensitizing molecule 30 enables the direct sequencing of RNA molecules without the need for an intermediate cDNA conversion step.

Since accuracy of correct nucleotide incorporation is of tantamount importance in DNA, RNA or cDNA sequencing, an alternative method for enhancing the detection of the specific incorporation of the correct dNTP or NTP would be to use analog dNTPs or NTPs which exacerbate the conformational dynamics of correct nucleotide incorporation thus ensuring accurate sequencing. Non-labeled analog dNTPs or NTPs which can be used to enhance the kinetic or dynamic discrimination of correct nucleotide incorporation are well known to one skilled in the art and include but are not limited to modifications of the purine and pyrimidine bases (i.e., at the C-4 and C-7 positions), the deoxyribose or ribose portions of the nucleotides, and the, alpha, beta and gamma phosphates of the dNTPs or NTPs including the use of tetra or penta-phosphates, with or without additional phosphate modifications.

Other methods of sequence accuracy enhancement that are compatible with the present invention that are known to one skilled in the art can be used including but not limited to reading the same template molecule multiple times. Other possibilities involve the use of a read twice format in which pyrophosphorolysis is used to read the same template molecule a second time.

An additional embodiment of the invention comprises a method for detecting the dynamics and kinetics of the single molecule sensing device. Any method for measuring changes in electrical conductance of the SWNT 12 can be used to monitor the single molecule sensing device 10. In the preferred embodiment, a bias difference of 100 mV is applied across the SWNT 12, and the current flowing through the conductor is measured as a function of time using circuitry 22 as illustrated in FIG. 1A. Chemical binding or recognition at the target-specific component of the sensitizing molecule 30 results in changes to the conductivity-modulating component of the sensitizing molecule 30, causing increases and decreases in the measured current. Multiple binding and unbinding events, which upon averaging comprise the chemical kinetics of the target-specific component, produce multiple current fluctuations that can be timed, counted, discriminated, analyzed or stored using signal processing techniques which are known in the art. The current fluctuations can consist of simple increases and decreases in a square-edged pattern. Alternately, the fluctuations can comprise any wavelet including shapes that are triangular, sinusoidal, or having any number of Fourier components. The amplitudes, durations, and shapes of these wavelets all encode the activity of the target-specific component and therefore can be analyzed using the computer 24 to uncover the kinetics of the binding and other mechanical and electronic degrees of freedom. Statistical analysis of these parameters provides insight into the kinetic variability, transitions, and intermediate chemical states of the target binding and unbinding processes. The degrees of freedom in the current signal distinguish among multiple similar target molecules that all bind to the same site, for example between a target molecule and an inhibitor molecule of the binding site. These degrees of freedom can also distinguish weak interactions such as molecule recognition that occur before true binding.

Another embodiment of the invention comprises the ability to distinguish and monitor either covalent or non-covalent binding of inhibitor molecules Inhibitors of protein function are commercially important as pharmaceutical agents, including anti-viral, anti-cancer and anti-bacterial therapeutics. The testing of effective inhibitors is a time-consuming and expensive process. The device 10 provides a new technique for directly monitoring protein function with single molecule resolution, while simultaneously probing the protein with any number of different candidate inhibitors. Using automated fluidic delivery systems well known in the art such as a flow cell, candidate inhibitor solutions can be delivered to the device one by one to identify inhibitors with the desired kinetic properties. Alternately, candidate inhibitors can be in mixtures, either as-synthesized or purposefully categorized by chemical structure or function or any other feature, in order to rapidly assay entire batches of candidate molecules.

It will therefore be seen that this invention is able to detect the dynamics and kinetics of a single sensitizing molecule. When the sensitizing molecule 30 is an enzyme, the kinetics and dynamics comprise rates of enzymatic turnover or rates of conformational movements. The technical advantage of the present invention is that the dynamics and kinetics of a single sensitizing molecule 30 can be detected, overcoming the problems of ensemble measurements that occur when multiple sensitizing molecules are present on the SWNT 12. Furthermore, the present invention overcomes the problems associated with prior methods of fabricating single molecule devices which create a defect site on the SWNT which is then functionalized a single sensitizing molecule. These advantages include the ability to detect the dynamics and kinetics of a single sensitizing molecule more precisely due to the lack of disruption of the $sp^2$ structure of the SWNT 12, a higher yield of functional devices in comparison with the lower functional device yield of defect site creation methods, a scalable fabrication method that can simultaneously produce many functional devices in parallel, and elimination of the chemical variability associated with disruption of the $sp^2$ structure.

The present invention provides a method of making a single molecule sensing device 10. The method includes forming at least one single-walled carbon nanotube 12 on a substrate 26 having first and second ends thereof connected, respectively, to a first electrode 14 and a second electrode 16. The single-walled carbon nanotube 12 sidewall of the device 10 is then non-covalently functionalized with at least one functional group of at least one linker molecule containing a plurality of functional groups. A single sensitizing molecule is functionalized with at least one the functional groups of the at least one linker molecule (e.g., the functional group that is not non-covalently functionalized with the SWNT 12).

Processes for synthesizing SWNTs are well known in the art, and the present invention includes any suitable process for synthesizing SWNTs. Preferably, suitable processes for synthesizing SWNTs include laser ablation, arc discharge, and chemical vapor deposition, all of which are well known in the art. Exemplary methods may be found, for example, in G. D. Nessim, "Properties, synthesis, and growth mechanisms of carbon nanotubes with special focus on thermal chemical vapor deposition," *Nanoscale* 2, 1306 (2010) and E. Joselevich, H. Dai, J. Liu, K. Hata, and A. H. Windle, in Carbon nanotubes, edited by A. Jorio, G. Dresselhaus, and M. S. Dresselhaus (Springer-Verlag, Berlin, 2008), Vol. 111, pp. 101, both of which are incorporated by reference.

More preferably, the method of SWNT synthesis and device fabrication comprises growth by chemical vapor deposition (CVD) directly onto wafer substrates, resulting in large areas of SWNTs with a uniform density of approximately 1 to 0.01 SWNTs/$\mu m^2$ and a diameter ranging from 0.6-2.4 nm. The substrate may be Si, $SiO_2$, or any other wafer used for semiconductor processing. This technique is well known in the art and comprises using any acceptable catalytic nanoparticle deposited onto the wafer; placement of the coated wafer substrates into a quartz tube furnace; reduction of the catalytic clusters at 940° C. in 1000 standard cubic centimeters per minute (sccm) $CH_4$ and 520 sccm $H_2$ in 3000 sccm Ar; and exposure to carbon feedstock at 940° C. in 1000 sccm $CH_4$ and 520 sccm $H_2$ in 3000 sccm Ar.

More preferably, the method of SWNT synthesis uses $Fe_{30}Mo_{84}$ catalyst nanoparticles; a preparation of a saturated solution of $Fe_{30}Mo_{84}$ catalyst nanoparticles in ethanol; a dilution to 1:1000 in ethanol; spin-coating of the dilute solution onto a clean wafer substrate surfaces at a rate of 150 rpm to provide a uniform and dilute coating of $Fe_{30}Mo_{84}$ catalyst particles; and oxidation of the catalytic clusters at 700° C. in air. See L. An, J. M. Owens, L. E. McNeil, and J. Liu, JACS 124 13688 (2002).

Following CVD, the wafers are processed in a cleanroom environment, electrically probed and characterized as 30% metallic and 70% semiconducting, and imaged by noncontact atomic force microscopy to confirm that only one SWNT is present in each device and that the device is free of particulate contaminants. The processing comprises optical lithography defining Ti electrodes on top of the randomly grown SWNTs with source-drain separations of 0.1 to 10 micrometers and the use of an undercut bilayer resist to improve liftoff and provide clean interfaces. More preferably, source-drain separations are 1 to 2 micrometers. As explained herein, optionally, the method of fabrication may include the step of defining an exposed window 20 within a protective cover 28 over the device 10 as explained above.

The exposed portion of the SWNT sidewall is non-covalently functionalized with the one or more functional groups of linker molecule(s) 28. Processes for non-covalently functionalizing a SWNT sidewall are well known in the art, and the present invention includes any suitable process for coating SWNTs with a dilute coating. Chen et al, *JACS* 123, 3838 (2001); Star et al., *Macromolecules* 36, 553 (2003); Star et al., *Nano Lett.* 3, 459 (2003). Achieving a dilute coating includes: (a) preparing a solution containing the linker molecule 28; (b) soaking the prepared devices 10 containing the exposed SWNT 12 in the prepared solution containing the linker molecules 28; (c) rinsing the devices 10 to remove excess linker molecules 28; (d) rinsing the device 10 to remove excess reagent; and (e) rinsing the device 10 under flowing de-ionized water.

Generally, the dimensions of the exposed portion of the SWNT 12 is chosen such that statistically, the devices 10 that are manufactured have only a small number (e.g., 1 to 1,000) of linker molecules 28 associated with the SWNT 12. The parameters that affect the number of linker molecules 28 (and thus potential sites for the attachment of sensitizing molecules 30) that are associated with the SWNT 12 include the length of the SWNT 12, the properties of the linker molecule 28, the incubation time, and the concentration of the linker molecules 28. Generally, a shorter incubation time or lower concentration of linker molecules 28 translates into fewer association sites on the SWNT 12.

After attachment of the linker molecules 28, the device is next exposed to a solution of sensitizing molecules 30. The properties of the sensitizing molecule 30, the particular attachment chemistry (e.g., maleimide-to-thiol), the properties of the solution (e.g., pH, temperature, salt and surfactant concentrations), the incubation time, and the concentration of the sensitizing molecules 30 all affect the yield with which sensitizing molecules will successfully bind to linkers. In practice, this yield can vary from 0.1% to 80%.

In order to select an appropriate length of SWNT 12 to be used with the device 10, the SWNT 12 can be examined with a microscope to see the spacing between adjacent sensitizing molecules 30. For instance, if this examination shows a distance of 1 µm, then the devices 10 can be produced having a protective window 18 with a width of around 1 µm to ensure that only a single sensitizing molecule 30 is functionalized on the SWNT 12.

Example 1

In this example, pyrene maleimide is used as the linker molecule. The pyrene functional group is known in the art to non-covalently functionalize with a SWNT sidewall. A solution of 1 mM N-(1-pyrenyl)maleimide in ethanol is prepared. Devices are soaked in the 1 mM N-(1-pyrenyl)maleimide in ethanol solution for 30 minute without agitation. Devices are washed with 0.1% polysorbate 20 in ethanol for 30 minutes with shaking to remove excess 1 mM N-(1-pyrenyl)maleimide. Devices are then rinsed in a solution of 50% polysorbate 20 (0.1%) in ethanol and 50% phosphate buffer (20 mM $Na_2HPo_4$, pH 7) for ten minutes without shaking to remove excess reagent. Devices are finally rinsed under flowing de-ionized water for 5 minutes.

The one or more functional groups of the linker molecules are functionalized with the one or more functional groups of the single sensitizing molecule. Processes for functionalizing one or more functions groups of a multifunctional linker molecule with one or more functional groups of a single sensitizing molecule are known in the art. See Z. Grabarek and J. Gergely, *Anal. Biochem.* 185, 131 (1990). Sensitizing molecules of the present invention include any molecule. Preferable sensitizing molecules include molecules that are chemically sensitive and that interact selectively with other molecules. More preferably, sensitizing molecules are proteins, DNA, RNA, ribozyme and/or aptamer, polysaccharide, or other biomolecule. Sensitizing molecules are well known in the art, and can comprise any sensitizing molecule suitable for use in the present invention.

Functionalization of the one or more functional groups of the multifunctional linker molecule with the one or more functional groups of the single sensitizing molecule comprises any method known in the art to functionalize two or more functional groups with each other. However, a limitation is that treatments that are known in the art to disrupt the non-covalent nature of the linkage between the linker molecule and the sidewall of the SWNT may not be used. Preferably, the functional groups used are those which are known in the art to exhibit "click chemistry," such as an azide and an alkyne, a thiol and an alkyne, and a thiol and a maleimide.

Example 2

The linker molecule is pyrene maleimide, with the pyrene functional group non-covalently attached to the SWNT sidewall. The single sensitizing molecule is a cysteine variant of T4 lysozyme which contains a single substituted cysteine as the mutation S90C to provide a reactive thiol for bio-conjugation. The cysteine variant of T4 lysozyme was synthesized by methods known in the art. A 54 µM solution of the cysteine variant of T4 lysozyme in phosphate buffer (20 mM $Na_2HPO_4$, pH 7) is prepared. Devices dilutely coated with the linker molecule pyrene maleimide non-covalently attached to the SWNT were soaked in the lysozyme solution at room temperature for 60 minutes without agitation. Devices were then soaked in wash buffer (5 mM KCl, 10 mM $Na_2HPO_4$, 0.05% polysorbate 20, pH 7) for 30 minutes with shaking to remove unattached lysozyme. Devices were finally rinsed under flowing de-ionized water for 5 minutes. These conditions lead to a density of approximately one T4 lysozyme molecule per micrometer of exposed SWNT.

Example 3

The linker molecule is pyrene maleimide, with the pyrene functional group non-covalently attached to the SWNT sidewall. The single sensitizing molecule is a cysteine variant of the Klenow fragment of DNA polymerase 1 (KF) derived from E. Coli, which contains a single inserted cysteine at site 790 to provide a reactive thiol for bio-conjugation. The cysteine variant of KF was synthesized by methods known in the art. A 0.2 mg/mL solution of the cysteine variant of KF in activation buffer (10 mM Tris-HCl, 10 mM $MgCl_2$, 50 mM NaCl, 1 mM DTT, pH 7.9) is prepared. Devices dilutely coated with the linker molecule pyrene maleimide non-covalently attached to the SWNT were soaked in the KF solution at room temperature for 60 minutes without agitation. Devices were then soaked in wash buffer (10 mM Tris-HCl, 10 mM $MgCl_2$, 50 mM NaCl, 0.1 mM TCEP, 0.1% polysorbate 20, pH 7.9) for 30 minutes with shaking to remove unattached KF. Devices were finally rinsed under flowing activation buffer for 5 minutes and stored in this solution until used. These conditions lead to a density of approximately one KF molecule per micrometer of exposed SWNT.

Example 4

The linker molecule is pyrene maleimide, with the pyrene functional group non-covalently attached to the SWNT sidewall. The single sensitizing molecule is a cysteine variant of protein Kinase A (PKA) which contains a single inserted cysteine at site T32C to provide a reactive thiol for bio-conjugation. The cysteine variant of PKA was synthesized by methods known in the art. A 52 µM solution of the cysteine variant of PKA in phosphate buffer (20 mM $Na_2HPO_4$, 100 µM TCEP, 2 mM ATP, 2 mM $MgCl_2$, pH 6.5) is prepared. Devices dilutely coated with the linker molecule pyrene maleimide non-covalently attached to the SWNT were soaked in the PKA solution at room temperature for 60 minutes without agitation. Devices were continuously rinsed with phosphate buffer (20 mM $Na_2HPO_4$, 0.05% Tween, 50 µM TCEP, pH 6.5) for 2 minutes and then placed in acidic phosphate buffer (20 mM $Na_2HPO_4$, pH 2.5) for 1 minute with shaking to remove unattached PKA. Devices were then rinsed with phosphate buffer (20 mM $Na_2HPO_4$, 100 µM TCEP, pH 6.5) for 5 minutes and stored in this solution until used. These conditions lead to a density of approximately one PKA molecule per micrometer of exposed SWNT.

The fully fabricated device is used by submerging the device in a gaseous or liquid environment. Temperature of the environment should be controlled and held constant and, in the case of liquids, so should the pH and electrochemical potential. An electrical bias is created and held constant between the source and the drain electrode. The current between the source, and the drain is measured over time and collected as control data points. The device is then exposed to a different chemical environment, and the levels of the current between the source and the drain is measured over time collected as experimental data points.

A small percentage (<10%) of devices fabricated using the more preferable method disclosed exhibit noise above normal values for the devices. This noise is due to SWNT defects or charge traps in the underlying substrate interacting with the surrounding environment. Those devices are to be discarded without further use.

In the embodiment of Example 2, the sensitizing molecule was lysozyme, and the chemical environment is 25 µg/ml peptidoglycan substrate in PBS buffer. The high ($I_{hi}$) and the low current values ($I_{lo}$) after the device is exposed to the peptidoglycan are measured over time. The parameters of the relative difference $\Delta I=(I_{hi}-I_{lo})/I_{lo}$ are statistically analyzed, and have been determined to be the most reliable way to analyze the conformational changes in the sensitizing molecule. With lysozyme, $I_{lo}$ is very similar to $I_{buffer}$, which suggests that $I_{lo}$ corresponds to the unbound and inactive configuration of lysozyme. $I_{hi}$, on the other hand, is substantially larger and is assigned to the mechanically-closed conformation of lysozyme around a bound peptidoglycan molecule. Electrical transitions from $I_{lo}$ to $I_{hi}$ indicate the hinge-like closure of lysozyme as it attempts to catalytically cleave a glycosidic bond of the peptidoglycan.

In the more preferred embodiment, oscillations in the electrical current between $I_{lo}$ and $I_{hi}$ occur with a broad distribution of stochastic durations that mirror the enzyme's activity. Sequences of ten or more oscillations can be categorized into one of two activity types, one slow and one fast. The slow oscillation corresponds to productive enzyme activity where the enzyme is successfully cleaving bonds of the peptidoglycan. The fast oscillations correspond to unproductive enzyme motion that does not cleave bonds. The amplitude of the signal $\Delta I$ is nearly the same in both slow and fast oscillations and is measured to be nearly constant, which supports a conclusion that the same range of molecular motion is being measured for both types of activity. This concurs with data from FRET which has previously proven that the range of mechanical motion in lysozyme is the same for both types of activity.

FIG. 2A illustrates an extended sequence of current fluctuation over 30 seconds, with the mean value highlighted using the setup of Example 2. FIG. 2B shows the instantaneous deviations from the mean current, coded into two different types of behaviors according to the two types of motion of the lysozyme protein being probed. FIG. 2C shows in detail the "fast switching" fluctuations of lysozyme protein doing nonproductive binding. FIG. 2D shows in detail the "slow switching" fluctuations of lysozyme protein doing catalytic processing. The fast oscillations occur on average 300 times per second. The slow oscillations occur on average 15 times per second. The exact rate of either oscillation varies from one conformation to another, so that long-duration measurements observe the conversion of the enzyme to different possible rates. In different minutes of measurement, the same protein can undergo slow oscillations varying from 10 to 80 times per second.

Figure 3A:
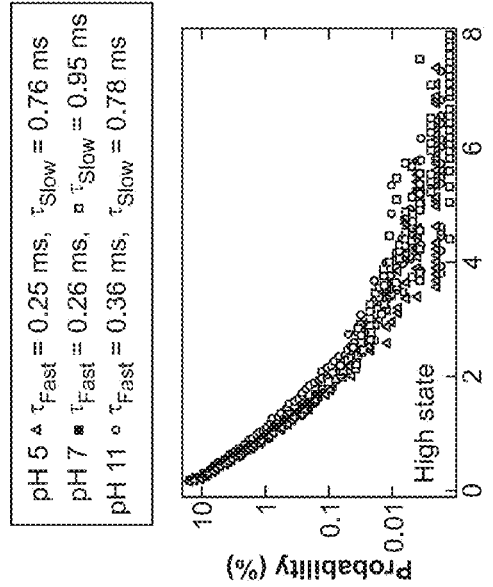
FIGS. 3A and 3B provide histograms of these events for $I_{hi}$ and $I_{lo}$ in both the fast and slow oscillating states.
Figure 3B:
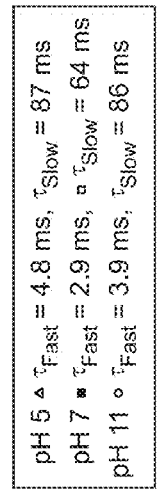
Figure 3C:
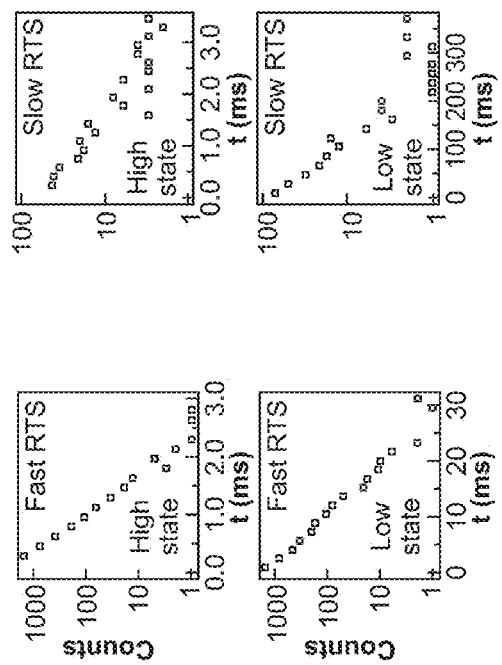
FIGS. 3C and 3D illustrate the change of these single-molecule parameters with different pH values.
Figure 3D:
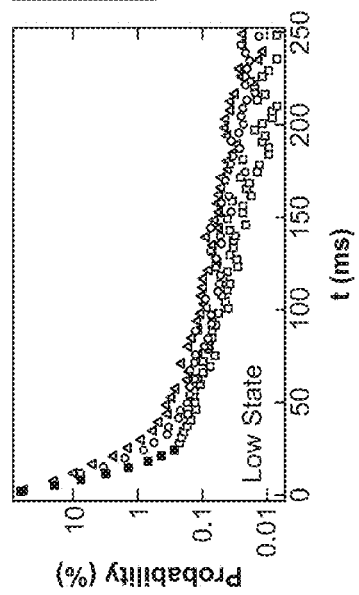

In either the fast or the slow oscillating state, single molecule resolution allows the statistical analysis of individual turnover events. FIGS. 3A and 3B provide histograms of these events for $I_{hi}$ and $I_{lo}$ in both the fast and slow oscillating states. FIGS. 3C and 3D illustrate the change of these single-molecule parameters with different pH values.

Figure 4:
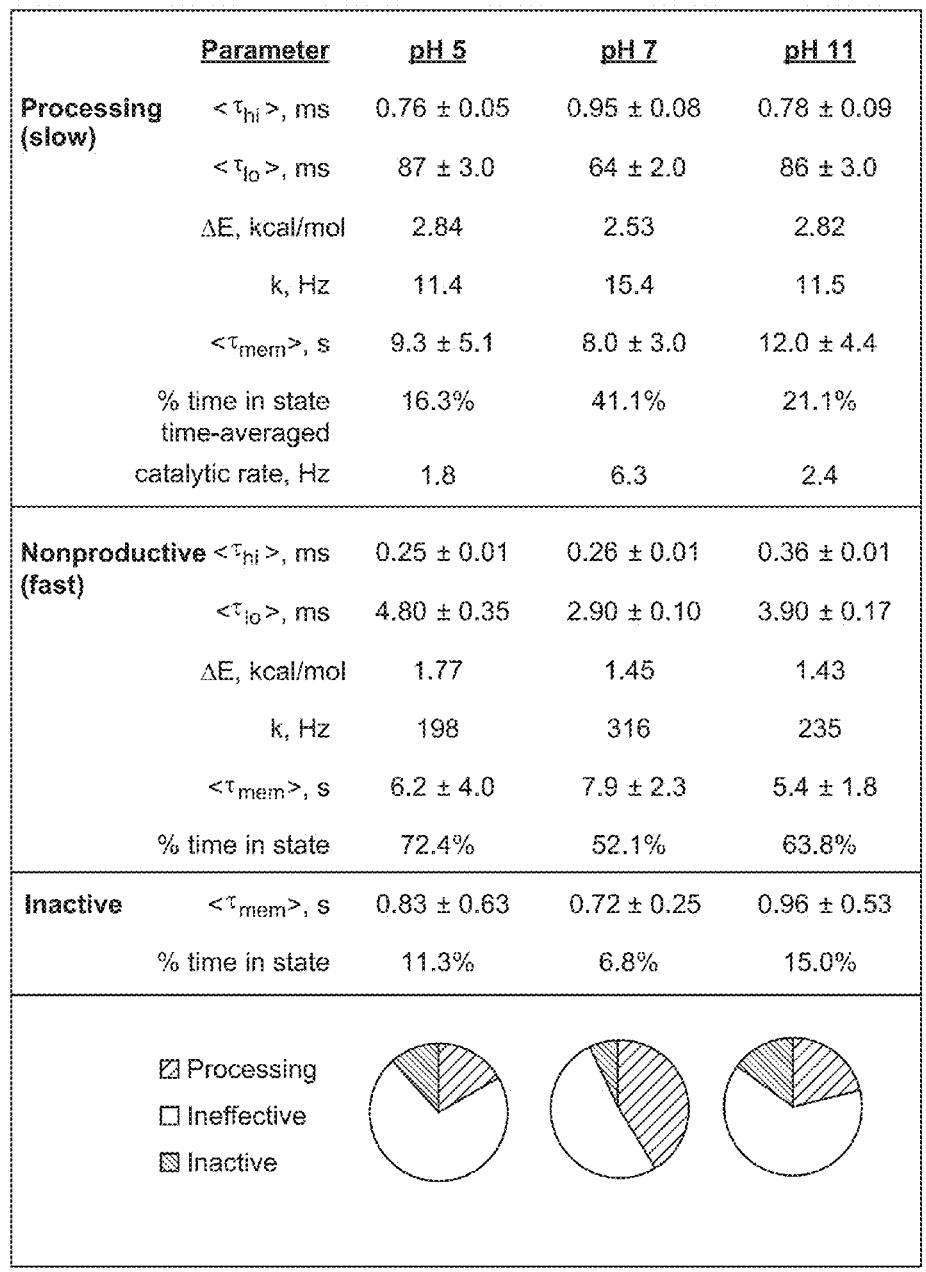
FIG. 4 summarizes the data with mean values of $\tau_{lo}$ and $\tau_{hi}$.

FIG. 4 summarizes the data with mean values of $\tau_{lo}$ and $\tau_{hi}$. Another figure of merit for each parameter is the statistical variance. From any large data set of individual $\tau_{lo}$ and $\tau_{hi}$ waiting times, not only can the mean value $<\tau>$ be calculated but also the variance $\sigma^2$ and normalized variance $r=\sigma^2/<\tau>^2$. Any single-step Poisson process has a variance $\sigma^2=<\tau>^2$, and the normalized variance $r=1$. On the other hand, values of $r<1$ indicate more complex processes, such as ones involving intermediate states. n identical Poisson processes in succession will produce a distribution of durations τ that have a variance r=1/n. Table 1 illustrates that the duration of $\tau_{lo}$ has a normalized variance r≈1 in both the fast and then slow states at the different pH values tested in the reported experiments. Thus, the transition from $I_{lo}$ to $I_{hi}$ is likely a simple, single-step Poisson process. The duration of $\tau_{hi}$ is significantly less than 1, though, indicating at least one intermediate step in the physical process associated with the $I_{hi}$ to $I_{lo}$ transition across the tested pH values.

TABLE 1

| | Parameter | pH 5 | pH 7 | pH 11 |
|---|---|---|---|---|
| Processing (slow) | $r_{hi}$ | 0.68 ± 0.15 | 0.74 ± 0.12 | 0.60 ± 0.15 |
| | $r_{lo}$ | 1.00 ± 0.18 | 1.06 ± 0.15 | 1.11 ± 0.23 |
| Nonproductive (fast) | $r_{hi}$ | 0.48 ± 0.10 | 0.43 ± 0.06 | 0.61 ± 0.08 |
| | $r_{lo}$ | 0.97 ± 0.13 | 0.99 ± 0.09 | 1.00 ± 0.10 |

Figure 5A:
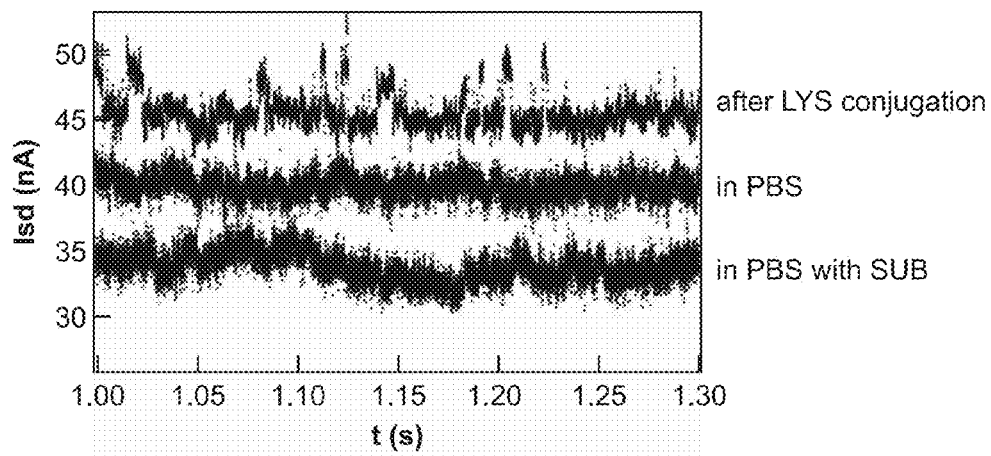
FIG. 5A shows the response of a pyrene-coated nanotube device, with and without peptidoglycan substrate (SUB), with a comparison to a complete lysozyme device.
Figure 5B:
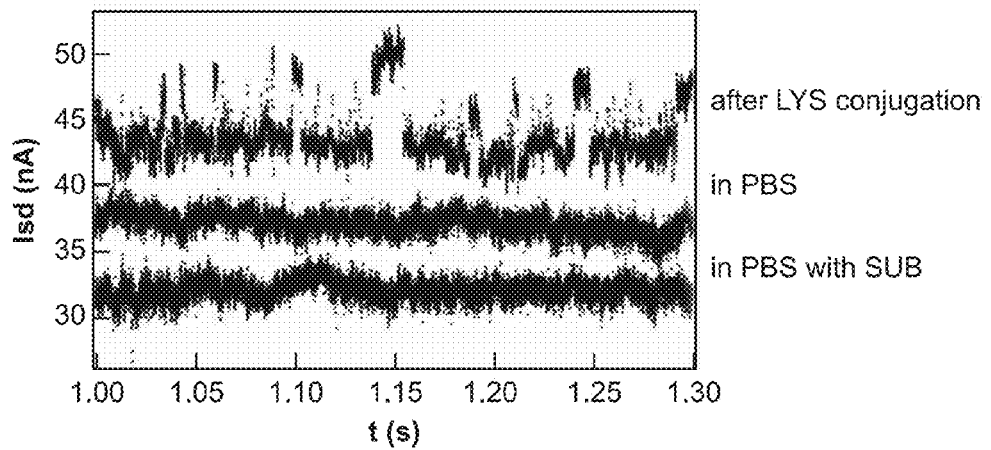
FIG. 5B shows the response of a bare nanotube device, with and without peptidoglycan substrate (SUB), with a comparison to a completed lysozyme device.

In one preferred embodiment, control measurements test for any dynamic response of the SWNT sidewall to the buffer, or to the substrate molecules used to probe the dynamics of lysozyme. As shown in FIG. 5A, un-functionalized devices showed no electronic signals that might be associated with dynamic interactions. No part of the noise power spectrum (DC –10 kHz) was sensitive to the presence of substrate or inhibitor molecules. Additional control measurements tested for any dynamic response of the linker-coated SWNT sidewall. This control is particularly relevant because the final devices consist of a pyrene-coated SWNT with single lysozyme attachments. In the absence of lysozyme, pyrene-coated SWNTs were measured in buffer, and in the same buffer solutions of substrate or inhibitor molecules used to probe the dynamics of lysozyme. As shown in FIG. 5B, pyrene-coated SWNTs showed no dynamic electronic response to the reagents when PBS is used as the buffer.

In general, the pyrene coating step tends to increase device conductance by 1-2 MΩ, whereas subsequent protein conjugation decreases the conductance. A cancellation is observed in FIG. 5A. Here a bare metallic SWNT device has nearly the same current level after the combination of pyrene coating and protein conjugation. On the other hand, FIG. 5B compares a pyrene-coated device before and after protein conjugation, in which case an offset is clearly observed. Note that FIGS. 5A and 5B are collected from two different devices of the more preferred embodiment that by coincidence have similar resistances of 2.0-2.5 MΩ.

As-fabricated devices of the more preferred embodiment have a wide range of contact resistances and, subsequently, initial device resistances $R_{pristine}$. Table 2 includes a few examples of the minimum achievable contact resistance, which for the diameter SWNT as fabricated by the CVD method discussed above is approximately 0.1-0.3 MΩ.

The increase in DC resistance $\Delta R_{coating}$ that occurs after pyrene coating and protein conjugation is also included on the table. For the low resistance devices, functionalization adds 0.8-2.7 MΩ to the device resistance (when measured in electrolyte biased at $V_g$=0). Low resistance metallic SWNTs and semiconducting SWNTs both show the same range of changes, which indicates that simple electrostatic shifts of the $I(V_g)$ characteristics cannot be the primary mechanism responsible for the increase. Instead, the $\Delta R_{coating}$ is interpreted to be to be extra scattering along the SWNT sidewall caused by the molecules. Three of twenty fabricated devices of the more preferred embodiment began with anomalously high $R_{pristine}$ values and consequently increase resistance much more dramatically upon functionalization.

Table 3 also tabulates mean values of the different current levels observed for each device. The current measured in PBS Buffer ($I_{buffer}$) can be compared to the $I_{hi}$ and $I_{lo}$ current values observed when the same device is switching. The general trend is for $I_{lo}$ to be quite similar to $I_{buffer}$, which suggests that $I_{lo}$ corresponds to the unbound configuration of lysozyme. $I_{hi}$, on the other hand, is substantially larger and is assigned to the bound substrate-lysozyme complex. Note that the inactive state described in the text is always inactive at the $I_{lo}$ current level, proving that the inactive state is also an unbound configuration. While this assignment is likely to be correct, the trend is not without apparent exceptions. Four of the devices fabricated with metallic SWNTs have $I_{lo} \approx I_{buffer}$, but in one device both currents $I_{hi}$ and $I_{lo}$ are substantially higher than would be expected from $R_{coated}$. Continuous measurements prove that $R_{coated}$ is a very poor benchmark, because its value varies in time and is dependent on surface charge transfer and the liquid electrolyte potential, strongly so for devices fabricated with semiconducting SWNTs.

Figure 6:
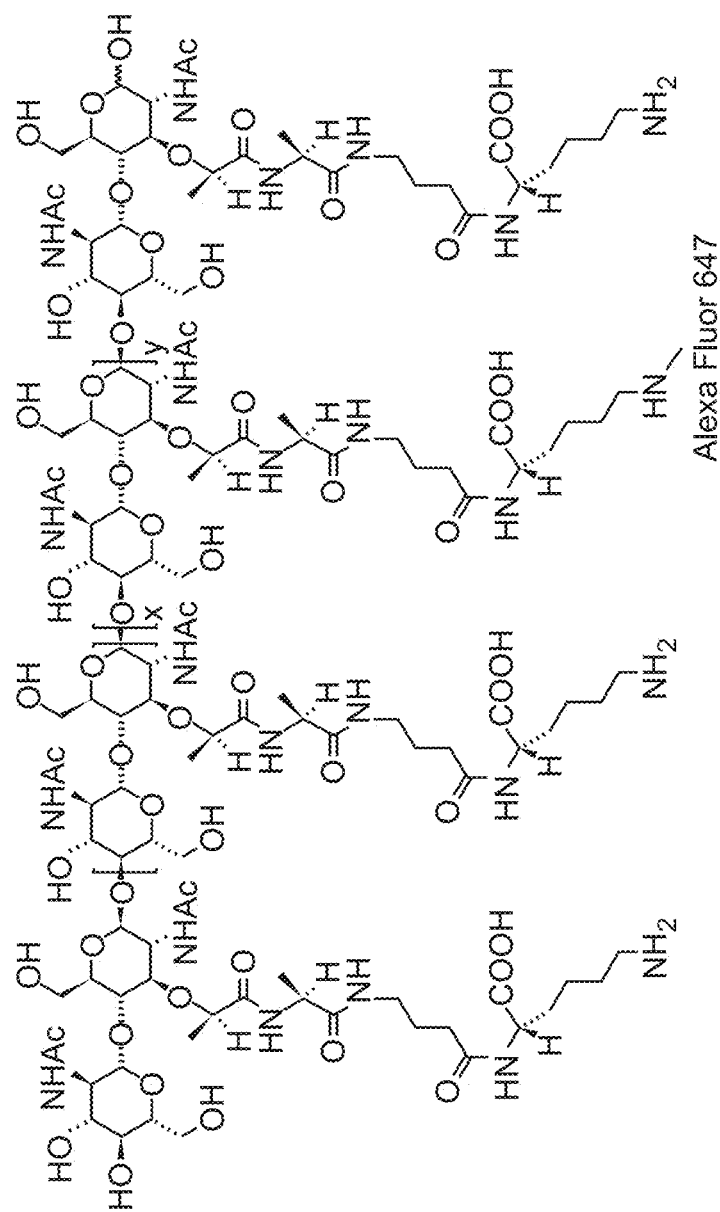
FIG. 6 shows the chemical structure of a modified peptidoglycan substrate that was synthesized without crosslinks.
Figures 7A, 7B, 7C, 7D, 7E:
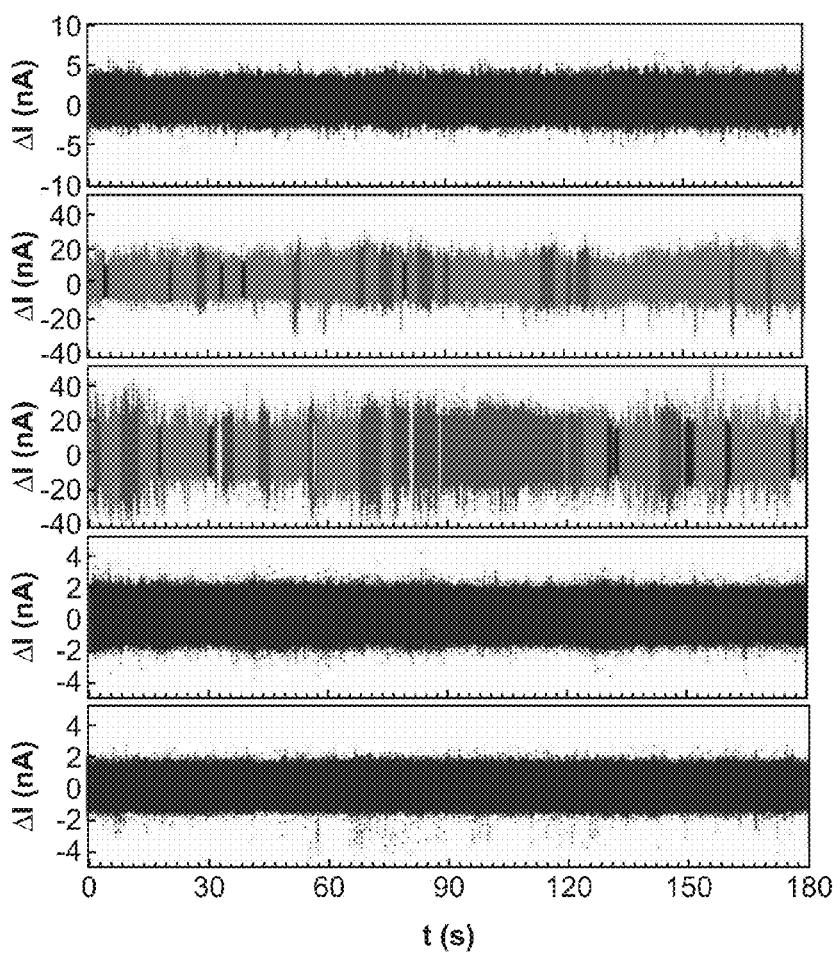
FIG. 7A illustrates the response of a lysozyme-based device without peptidoglycan substrate.
FIGS. 7B and 7C show one lysozyme device being tested against solutions containing modified and unmodified peptidoglycan, respectively.
FIG. 7D shows the response of a control device made with a chemically inactive E11H lysozyme mutation.
FIG. 7E shows the response of a control device made with a chemically inactive T26E lysozyme mutation.

A usefulness of the single molecule sensing device is the ability to directly observe changes in molecule function or activity in response to different target analytes. FIG. 6 shows the chemical structure of a modified peptidoglycan substrate that was synthesized without crosslinks. FIG. 7A illustrates the response of a lysozyme-based device without peptidoglycan substrate. FIGS. 7B and 7C show one lysozyme device being tested against solutions containing modified and unmodified peptidoglycan, respectively. FIG. 7D shows the response of a control device made with a chemically inactive E11H lysozyme mutation. FIG. 7E shows the response of a control device made with a chemically inactive T26E lysozyme mutation.

The preferred embodiment of the device transduces any event that drives molecular motion, and it is therefore sensitive to both covalent and non-covalent chemical activities. This is demonstrated in FIGS. 7A-7E and FIG. 8. The slow current oscillations in the signals in FIGS. 7A-7C report effective catalytic (covalent) activity, while the fast current

TABLE 2

| # | Type | $R_{pristine}$ (MΩ) | $R_{coated}$ (MΩ) | $\Delta R_{coating}$ (MΩ) | $I_{PBS}$ (nA) | $I_{lo}$ (nA) | $I_{hi}$ (nA) | $\Delta I_{RTS}$ (%) | $dI/dV_g$ (%/V) | $\Delta V_g(V)$ calc |
|---|---|---|---|---|---|---|---|---|---|---|
| 1 | s-SWNT | 0.28 | 1.2 | 0.9 | 36* | 40* | 48* | +20% | 95 | 0.21 |
| 2 | s-SWNT | 0.38 | 1.5 | 1.1 | 87 | 103 | 122 | +18% | 88 | 0.21 |
| 3 | s-SWNT | 0.34 | 3.0 | 2.7 | 5.65 | 7 | 10.5 | +50% | 266 | 0.19 |
| 4 | s-SWNT | 17.6 | 56 | 38 | 2.5 | 2.8 | 2.9 | +4% | 20 | 0.20 |
| 5 | s-SWNT | 26.1 | 40 | 14 | 7.0 | 7.2 | 8.2 | +14% | 70 | 0.20 |
| 6 | m-SWNT | 0.10 | 1.4 | 1.3 | 78 | 80 | 82 | +3% | 18 | 0.16 |
| 7 | m-SWNT | 0.30 | 2.0 | 1.7 | 54 | 54 | 58 | +7% | 46 | 0.15 |
| 8 | m-SWNT | 0.35 | 2.6 | 2.2 | 42 | 45 | 50 | +10% | 54 | 0.19 |
| 9 | m-SWNT | 1.0 | 1.8 | 0.8 | 55 | 80 | 83 | +4% | 21 | 0.18 |
| 10 | m-SWNT | 3.0 | 30 | 27.1 | 3.5 | 3.3 | 4.9 | +47% | 235 | 0.20 | oscillations report changes in the non-catalytic, non-covalent interactions between lysozyme and its substrate.

Figure 8:
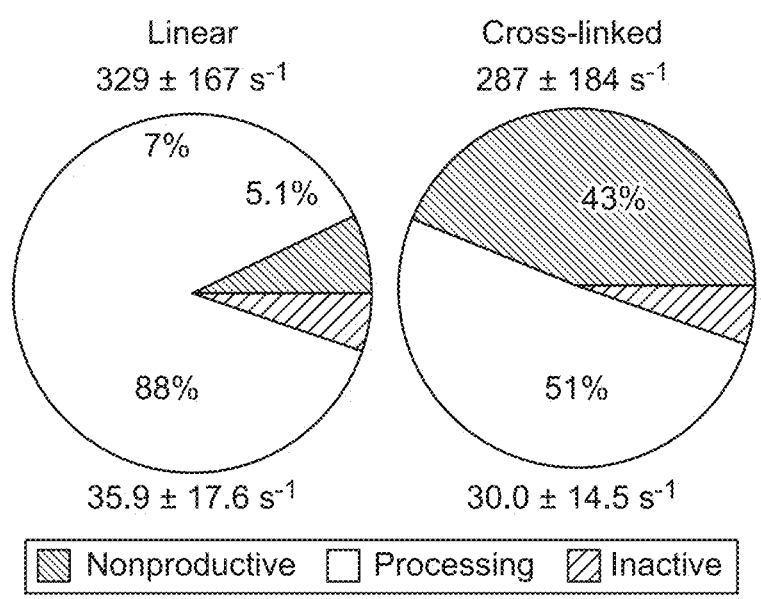
FIG. 8 compares the enzymatic processing modes of lysozyme upon two different types of peptidoglycan substrate.

FIG. 8 summarizes the results of analyzing both data sets using the metrics described above. Lysozyme spends 88% of its time processing when the substrate is the linear version without crosslinks. This processing effectiveness decreases substantially to 51% when the substrate contains crosslinks, directly indicating the consequence of the additional chemical bond in the substrate molecule.

In the more preferred embodiment, changes in the design of the conductivity-modulating component of the sensitizing molecule can increase, decrease, or reverse the sign of the electrical signal that results from chemical activity. In the embodiment using lysozyme as the sensitizing molecule, measurements prove that the signal can be wholly controlled using only two charged amino acids, K83 and R119, which are near the SWNT attachment component of the molecule. This conclusion was reached by measuring the response of a lysozyme device in different salt concentrations and by fabricating devices with one of seven different active lysozyme substitutions of the two residues.

Figure 9A:
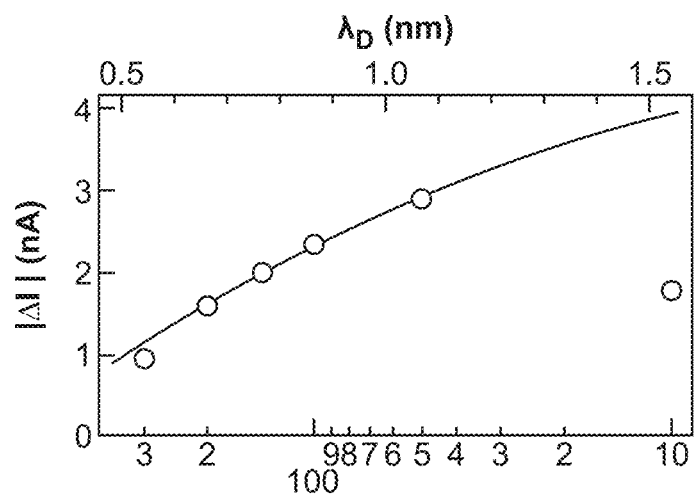
FIG. 9A shows the magnitude of response for a lysozyme single molecule sensing device as a function of salt concentration (bottom axis) or Debye length (top axis).
Figure 9B:
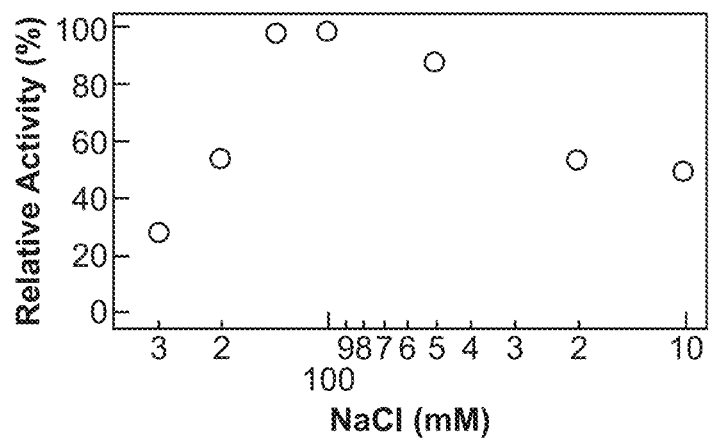
FIG. 9B shows the bulk activity of an ensemble of lysozyme molecules, confirming the activity over the same range of salt concentrations.

The role of the salt concentration in the surrounding fluid is to shield the SWNT conductor from most of the electric fields of the lysozyme's surface charges. FIG. 9A illustrates the electrical response of lysozyme devices to measurements in NaCl concentrations varying from 10 mM to 300 mM (in 10 mM phosphate buffer). The line through the data in FIG. 9A is a fit to the Debye-Huckel expression for electrolyte shielding. The fit determines that most of the lysozyme is fully shielded by the surrounding electrolyte, and that the SWNT conductor is only responding to surface charges within 1 to 2 nm of the SWNT attachment site. This small distance is notable given that the lysozyme molecule has physical dimensions of 5 to 7 nm, and that the active site for peptidoglycan catalysis is located 3.1 nm from the SWNT attachment site. Thus, the measurement identifies the critical role of the conductivity-modulating component of the lysozyme molecule and its physical separation from the chemically-selective component of the same molecule. FIG. 9B illustrates the bulk activity of an ensemble of lysozyme molecules, confirming activity over the same range of salt concentrations.

Figure 10:
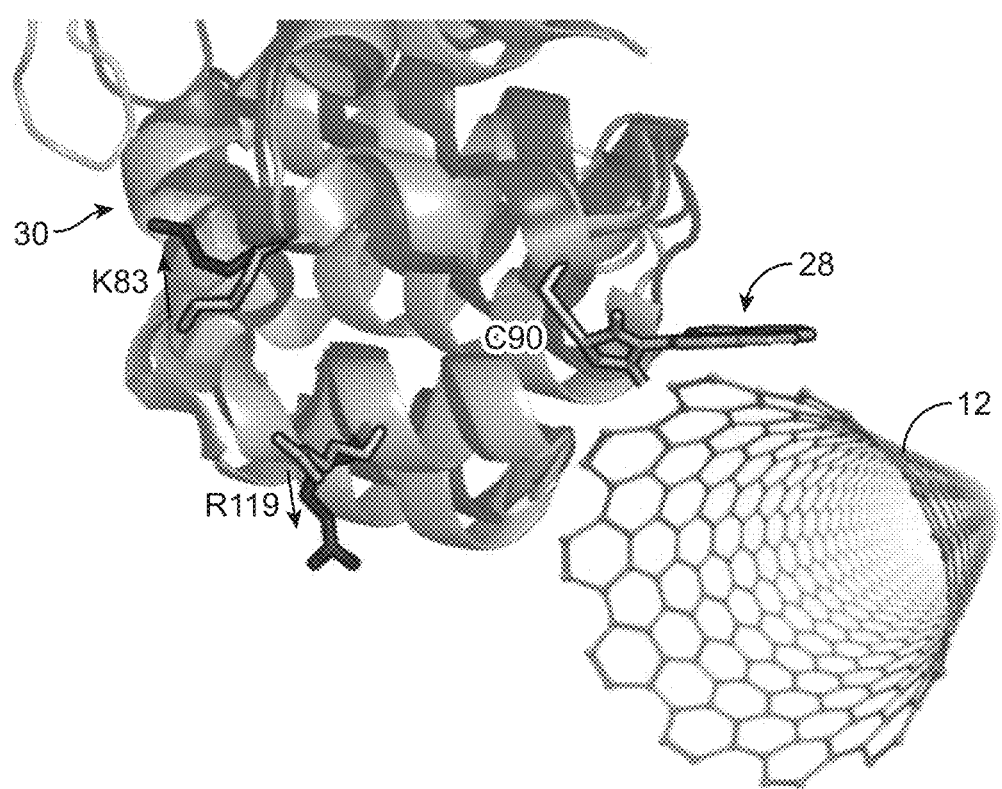
FIG. 10 shows a schematic diagram of a pyrene-maleimide linker molecule attaching a lysozyme enzyme to a SWNT, and depicts the mechanism of the conductivity-modulating component of the lysozyme.

FIG. 10 depicts the geometry of this embodiment. A pyrene-maleimide molecule is shown with the pyrene ring non-covalently attached to the SWNT 12 and the maleimide group covalently bound to the C90 site of the lysozyme variant. Two charged amino acids, K83 and R119, are found within 2 nm of this attachment site, and both undergo substantial motions of 0.1 to 0.2 nm when the lysozyme opens and closes upon addition of peptidoglycan. Substrate binding drives large scale conformational changes that affect the entire molecule, not just its binding site. Thus, a mechanical or allosteric linkage exists through the protein structure whereby activity of the chemically-functional, chemically-selective site of lysozyme can mechanically affect the position of surface charges near the SWNT. The two surface charges and their movement constitute the conductance-modulating component of the lysozyme molecule when the attachment is at the 90C site.

Figure 11:
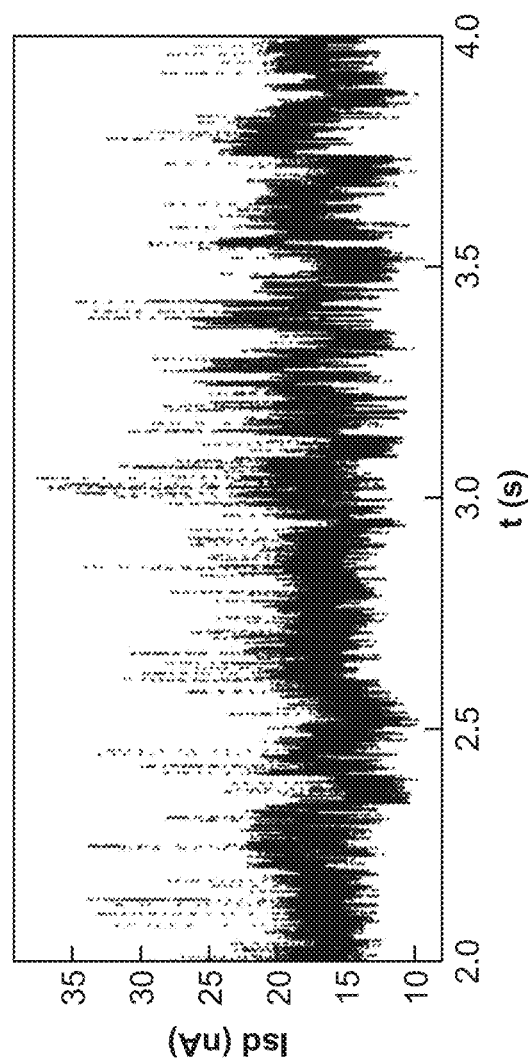
FIG. 11 shows the response from a lysozyme device with its SWNT attachment site located at the S36 position instead of S90.

The portion of the lysozyme molecule comprising the conductance-modulating component is the set of surface charges that have both of the following properties: (a) charges closer than 2 Debye-Huckel lengths from the SWNT conductor, so that their effects are not primarily shielded by the electrolyte, and (b) charges that move in coordination with motions of the sensitizing molecule or the activity of its chemically-specific component. Lysozymes attached via cysteines at alternate sites therefore have different conductance-modulating components. A different, S36C variant of pseudo wild-type lysozyme reproducibly produced multi-leveled signals such as those shown in FIG. 11. The signal from this variant is more complex than from the S90C variant of the preferred embodiment, even though both variants exhibited similar catalytic activities.

To demonstrate that the two amino acids K83 and R119 constitute the conductivity-modulating component of the lysozyme molecule, the two, positively-charged sidechains underwent targeted mutations into either neutral alanines or negatively charged glutamic acid residues. Seven active variants of S90C lysozyme were synthesized and measured in single molecule sensor devices. FIG. 12A shows the $I_{hi}$ and $I_{lo}$ values from a positively-charged variant processing peptidoglycan. FIG. 12B shows the same for a negatively-charged variant, in which the roles of the two current levels are reversed. FIGS. 13B and 13C summarizes the signal amplitudes obtained from seven different S90C variants (seen in FIG. 13A) having net charges covering the range of N={+2, +1, 0, −1, −2} electrons. The results are in excellent agreement with an electromechanical mechanism in which the SWNT conductor responds to the electric fields generated by the two targeted amino acids.

The successful result of modifying the conductivity-modulating component of lysozyme demonstrates an effective set of design rules for predicting and controlling the signal from the single molecule sensor device. Whenever X-ray crystal structures are available for sensitizing molecules in two or more conformations of interest, the structural data can be used to identify the locations of significant movement and their net charge. Sequence information and structural prediction could also guide such device design. Subsequently, protein mutagenesis can be used to enhance or modify that net charge. Protein mutagenesis can also introduce a chemical group nearby for one of the linker molecule or other SWNT attachment schemes. Alternately, an attachment scheme can be selected that makes use of the existing chemical groups near such a location. It is important to note that an effective SWNT attachment site does not need to be located near the chemically-active binding site, and attachments at such positions are likely to negatively impact chemical function and kinetics.

In the preferred embodiment, both metallic and semiconducting carbon SWNTs produce comparable signal-to-noise ratios (SNRs). The SNR is not substantially improved by seeking a particular type of SWNT.

Figure 14A:
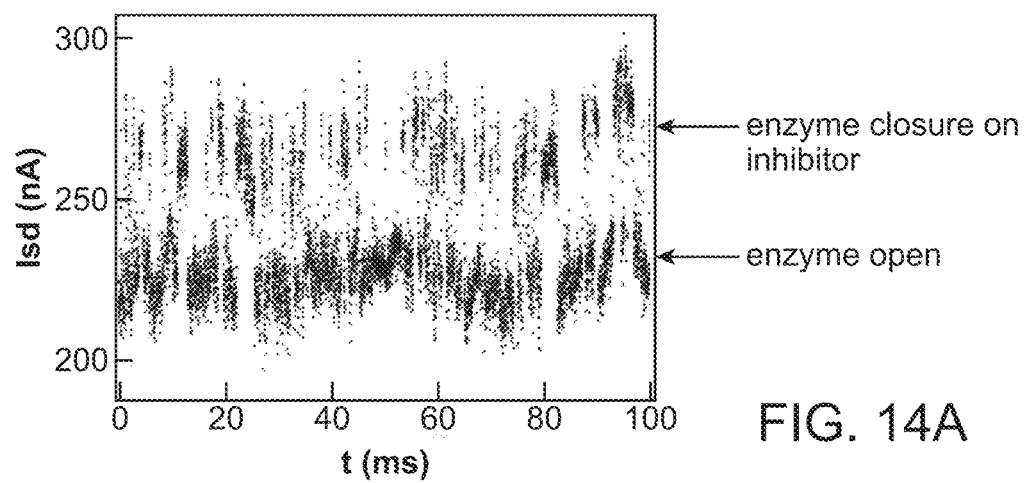
FIG. 14A shows the response of a lysozyme device to a non-covalent inhibitor.
Figure 14B:
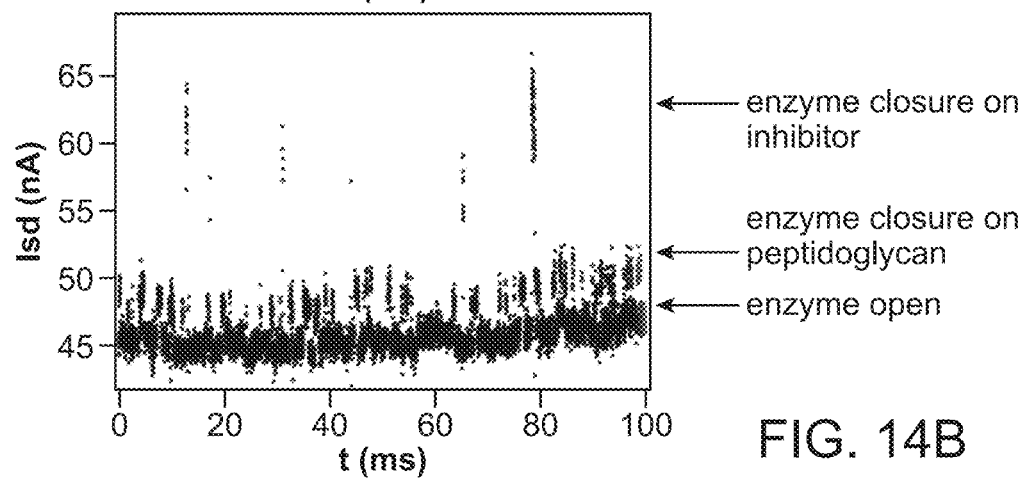
FIG. 14B shows the response of a lysozyme device to a combination of both non-covalent inhibitor and peptidoglycan substrate, with different signal amplitudes generated by each.

The sensitivity to non-covalent interactions enables the direct monitoring of chemical inhibition. In one preferred embodiment, inhibitor molecules can interact with lysozyme's catalytically-active site and interfere with the enzymatic processing of peptidoglycan. The trivial case of permanently-bound inhibitors quenches the signal of a lysozyme device. The more interesting case of weakly-interacting, non-covalent inhibitors produces dynamic signals in I(t). Two such inhibitors were tested, indole-3-propionic acid (I3P) and a custom-synthesized, 8-mer peptide isolated using phage display ($H_2N$-LRCPWCYM-$CONH_2$). Interactions with both inhibitors were clearly observed in the electronic I(t) signals. FIG. 14A shows the results of probing a lysozyme device with 10 mM I3P, where the baseline $I_{lo}$ current of the device is interrupted by brief pulses $I_{hi}$. Notable features of these pulses are that they are distinguishable in amplitude ($\Delta I$=+20%) and duration ($\tau_{hi}$<1 ms) from the signals produced by peptidoglycan. FIG. 14B shows a different lysozyme device being simultaneously exposed to both peptidoglycan and I3P inhibitor. Interactions with I3P were sufficiently distinct from the peptidoglycan substrate that two different signals are easily distinguishable. Thus, the preferred embodiment is able to simultaneously observe the kinetic effects of inhibition on peptidoglycan processing, even substrate and inhibitor both compete for the same binding site. The two-level interactions with I3P have been observed continuously for 10 minutes with no sign of pauses or decreased activity.

In the preferred embodiment of Example 3, the sensitizing molecule is DNA polymerase 1 (Klenow Fragment, KF), and the chemical environment is a 100 nM solution of deoxyribonucleic acid (DNA) template and 100 μM deoxyribonucleotide triphosphate (dNTP) in buffer (50 mM NaCl, 10 mM $MgCl_2$, 20 mM Tris, 10 mM dithiothreitol, pH 7.8). As before, high ($I_{hi}$) and low ($I_{lo}$) current values are observed during chemical activity and monitored in time. With KF, $I_{hi}$ is very similar to $I_{buffer}$, which suggests that $I_{hi}$ corresponds to the unbound and inactive configuration of the enzyme. Transient pulses to a smaller current $I_{lo}$ occur in the presence of chemical activity, which in this system requires the simultaneous presence of DNA template, dNTP to be incorporated, and $Mg^{2+}$ ions. Electrical transitions from $I_{hi}$ to $I_{lo}$ indicate the incorporation of one nucleotide into the template and can be statistically analyzed in the same ways as described for lysozyme.

Figure 15A:
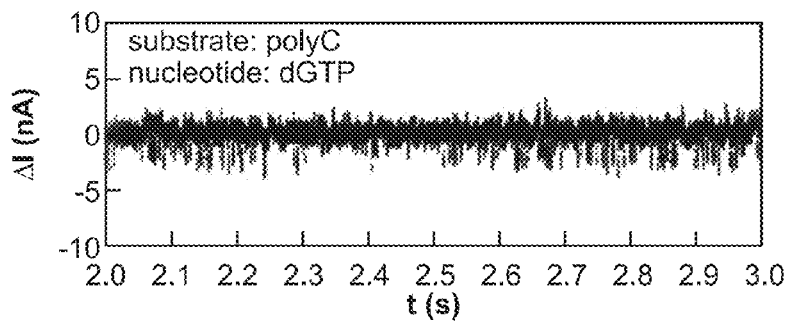
FIG. 15A shows 1 typical second of response from a DNA polymerase I device measured in buffer solution with polyC substrate and dGTP nucleotides.
Figure 15B:
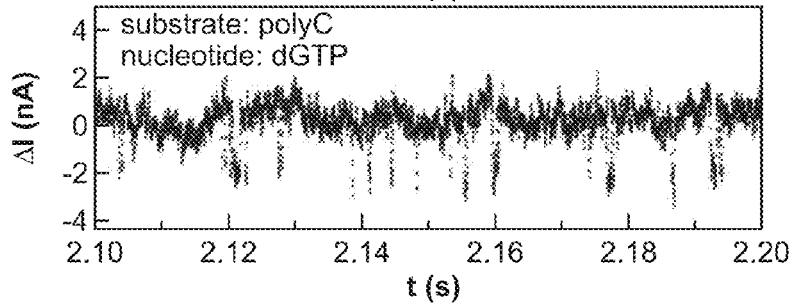
FIG. 15B shows individual processing events on a 0.1 s time axis from a DNA polymerase I device measured in buffer solution with polyC substrate and dGTP nucleotides.
Figure 15C:
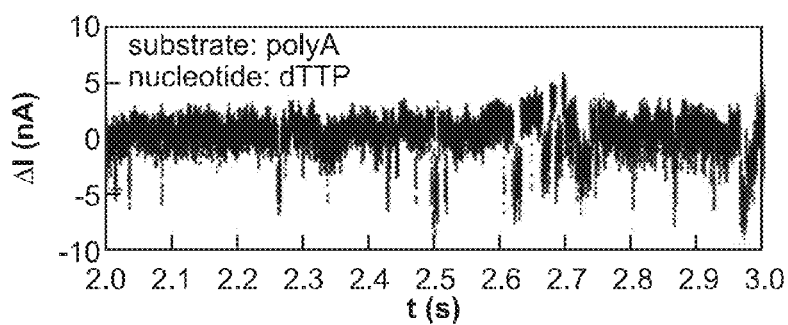
FIG. 15C shows 1 typical second of response from a DNA polymerase I device measured in buffer solution with polyA substrate and dTTP nucleotides.
Figure 15D:
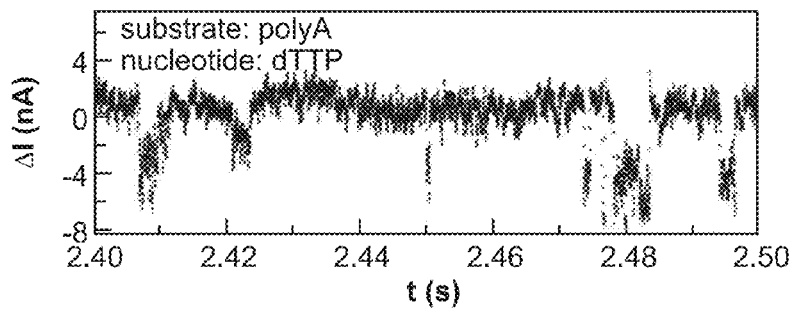
FIG. 15D shows individual processing events on a 0.1 s time axis from a DNA polymerase I device measured in buffer solution with polyA substrate and dTTP nucleotides.

FIGS. 15A-15D illustrate the signals produced by this embodiment when measured in buffer with different combinations of substrate and nucleotides. FIGS. 15A and 15B show the response of a KF sensitizing molecule measured with at least 10 nM polyC substrate and an excess of dGTP on 1 second and 0.1 second time scales, respectively. In the latter graph, the timing and amplitude of individual events are clearly resolved. Each event represents the addition of the nucleotide dGTP to the polyC substrate. FIGS. 15C and 15D show the same device measured with at least 10 nM polyA substrate and an excess of dTTP on identical time scales. On average, the individual events in FIG. 15D have shorter durations and higher amplitudes than the events in FIG. 15B. When either substrate or nucleotides are absent in these measurements, no transitions to $I_{lo}$ are observed. Again, with reference to FIG. 15D, each event (dip in measured current) represents the addition of the nucleotide dTTP to the poly A substrate.

Figure 16A:
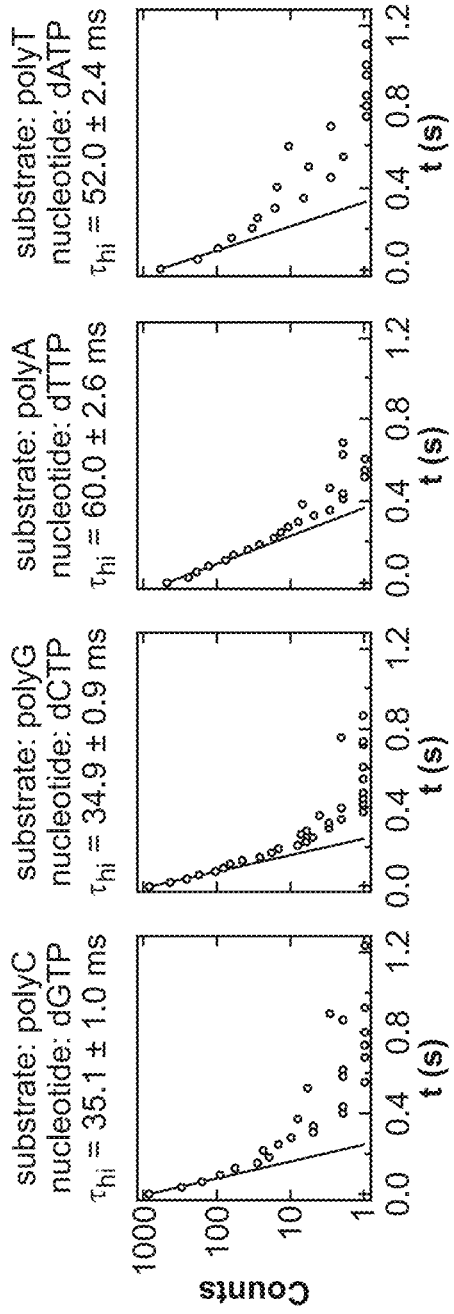
FIG. 16A compares single-molecule probability distributions for $\tau_{hi}$ from all four DNA bases, as measured by a DNA polymerase I device.
Figure 16B:
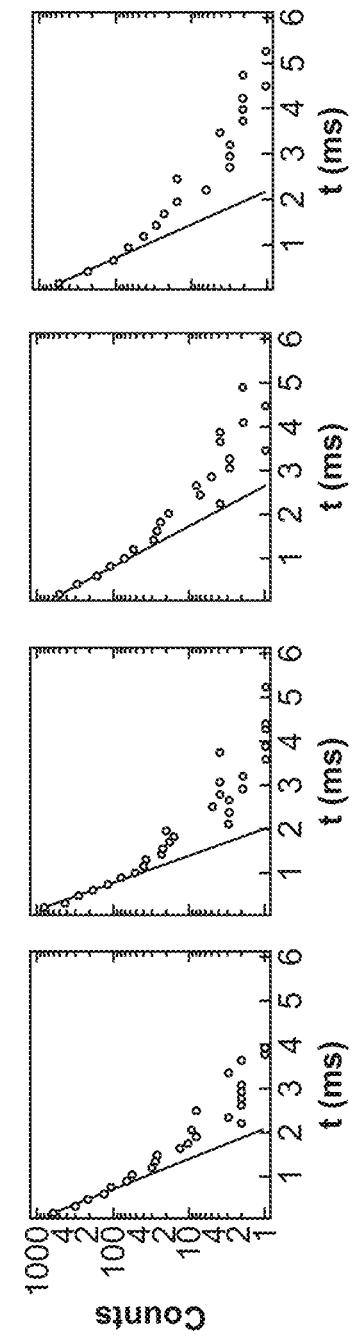
FIG. 16B compares single-molecule probability distributions for $\tau_{Io}$ from all four DNA bases, as measured by a DNA polymerase I device.
Figure 16C:
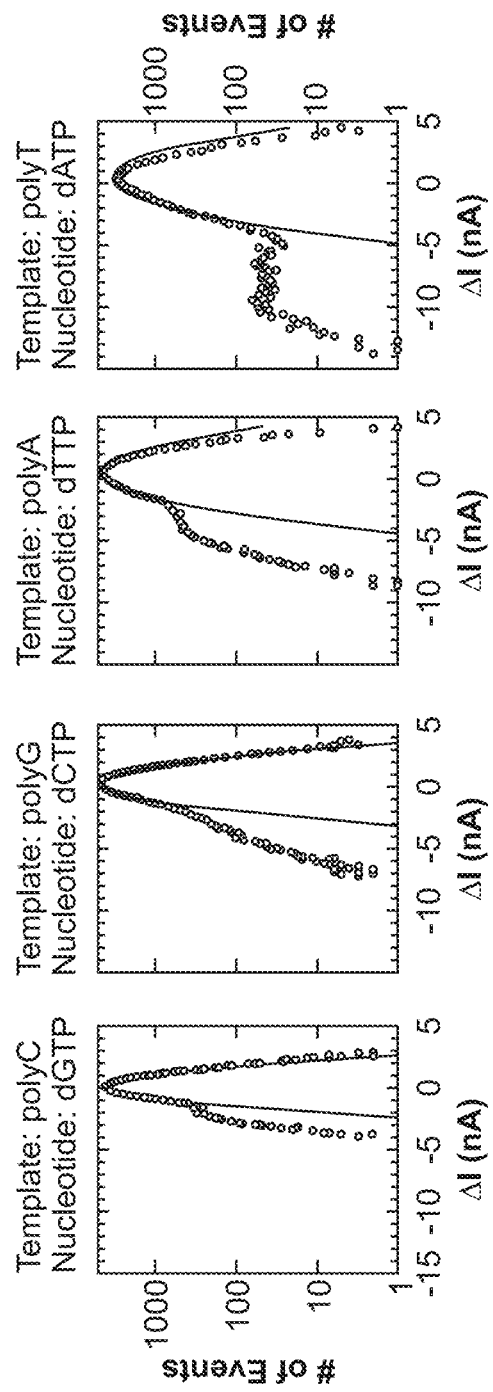
FIG. 16C compares the distribution of signal amplitudes from all four DNA bases, as measured by a DNA polymerase I device.

The device is capable of distinguishing all four types of base incorporation, and allows large numbers of individual events to be analyzed statistically. FIGS. 16A-16C illustrates typical types of analysis performed on data generated by a single KF protein in the presence of different combinations of DNA substrates and nucleotides. FIG. 16A plots the single-molecule probability distributions for the $I_{hi}$ states of all four bases A, C, G, and T. Fits to each distribution are shown as solid lines and determine the mean value of $\tau_{hi}$ for each base pair. FIG. 16B plots the distributions for the four $I_{lo}$ states and gives the values of $\tau_{lo}$. The values of $\tau_{hi}$ are much longer than $\tau_{lo}$ and therefore they determine the overall turnover rate of the KF protein for a particular type of base. The data distinguish dGTP and dCTP as having shorter incorporation times and faster turnover rates than either dTTP or dATP. Table 3 below illustrates turnover rate, $\tau_{hi}$, $\tau_{lo}$ for four different nucleotides. The incorporation event itself has a duration represented by the time $\tau_{lo}$, and here three of the bases are indistinguishable with dTTP being distinctly slower.

TABLE 3

| substrate | nucleotide | turnover rate (1/s) | τ hi (ms) | τ lo (ms) |
|---|---|---|---|---|
| polyT | dATP | 14.4 ± 2.9 | 71.4 ± 14.3 | 0.33 ± 0.08 |
| polyA | dTTP | 16.0 ± 2.9 | 63.7 ± 11.4 | 0.42 ± 0.09 |
| polyG | dCTP | 26.2 ± 4.4 | 39.0 ± 5.6 | 0.32 ± 0.07 |
| polyC | dGTP | 28.5 ± 3.5 | 38.0 ± 5.8 | 0.33 ± 0.06 |

FIG. 16C shows the distributions of ΔI(t) signal amplitudes obtained from measurements on the four types of base pairs. Each amplitude distribution is centered around a large peak at 0 nA, corresponding to the enzyme-open, $I_{hi}$ portion of the I(t) signal. The $I_{hi}$ portion of the distribution has been fit to a single Gaussian peak indicated by a solid line. Data outside of this peak correspond to $I_{lo}$ events, which are counted and histogrammed based on the magnitude ΔI of each event. The four graphs are ordered from smallest to largest average ΔI value. Incorporation of dGTP exhibits the smallest amplitude and incorporation of dATP has the largest.

In this embodiment and using unmodified nucleotides, neither the timing distributions nor the amplitude distributions are sufficient to distinguish one type of base pair from another. However, the two parameters used in combination identify individual bases with a much higher accuracy than either parameter alone. In combination with additional signal analysis, base identification can be improved further. Additional signal parameters of interest include the slopes of transition edges between $I_{hi}$ and $I_{lo}$ and fluctuations within the $I_{lo}$ incorporation step. The use of modified nucleotides is another strategy for distinguishing individual base pairs that is well known in the art. By providing an environment of modified nucleotides, the signal parameters described here can be made even more distinct.

In the embodiment of Example 4, the sensitizing molecule is protein Kinase A (PKA), and the chemical environment is a 100 μM solution of the synthetic peptide substrate Kemptide, in a solution of 2 mM ATP and buffer (100 mM of 3-(N-morpholino)propanesulfonic acid (MOPS), 9 mM $MgCl_2$, pH 7.0). As before, changes in the current values are observed during chemical activity and monitored in time. With PKA, $I_{hi}$ is very similar to $I_{buffer}$, which suggests that $I_{hi}$ corresponds to the unbound or inactive configuration of the enzyme. Transient pulses to a smaller current $I_{mid}$ occur in the presence of ATP without Kemptide, indicating the formation of the intermediary complex between PKA and ATP. When both ATP and binding substrate are present in solution, as is required for catalytic activity, a still smaller current $I_{lo}$ is observed.

Figure 17A:
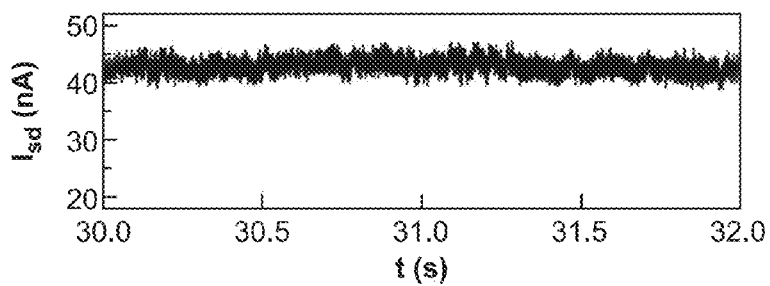
FIG. 17A shows 2 typical seconds of response from a PKA device measured in buffer solution without ATP or Kemptide substrate.
Figure 17B:
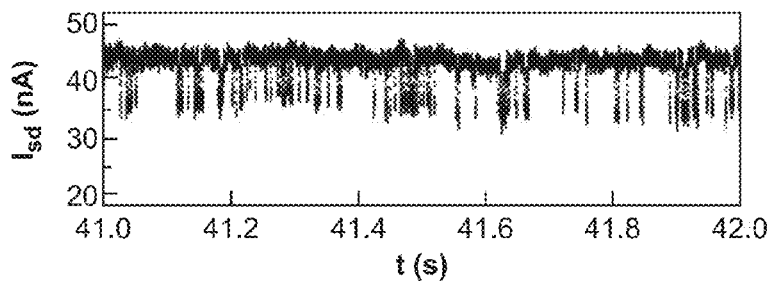
FIG. 17B shows 1 typical second of response from a PKA device measured in buffer solution with ATP but without Kemptide substrate.
Figure 17C:
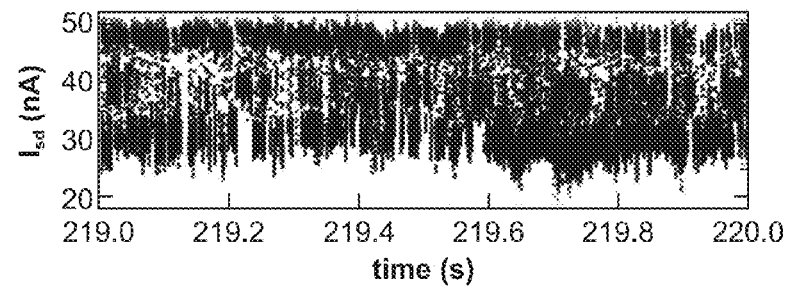
FIG. 17C shows 1 typical second of response from a PKA device measured in buffer solution with ATP and Kemptide substrate.
Figure 17D:
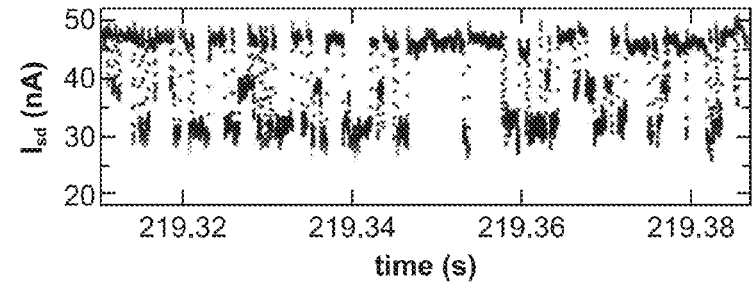
FIG. 17D shows individual processing events on an 80 ms time axis for a PKA device in buffer solution with ATP and Kemptide substrate.

FIGS. 17A-17D illustrates the signals produced by this embodiment. FIG. 17A shows the typical background noise and average level $I_{hi}$ observed from the PKA sensitizing molecule when measured in buffer solution. FIG. 17B shows the transitions between $I_{hi}$ and $I_{med}$ that occur when ATP is added to the buffer. FIG. 17C shows transitions between all three levels, $I_{hi}$, $I_{med}$ and $I_{lo}$ that occur when both ATP and Kemptide substrate are present. FIG. 17D shows just 80 ms of the same data, to highlight the individual events. All four panels of FIGS. 17A-17D use the same y-axis scale to allow direct comparisons.

Figure 18A:
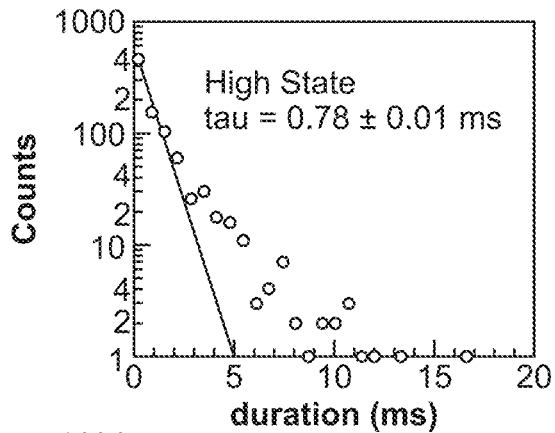
FIG. 18A shows the single-molecule probability distribution function for $I_{hi}$, the unbound configuration, during Kemptide processing by a PKA device.
Figure 18B:
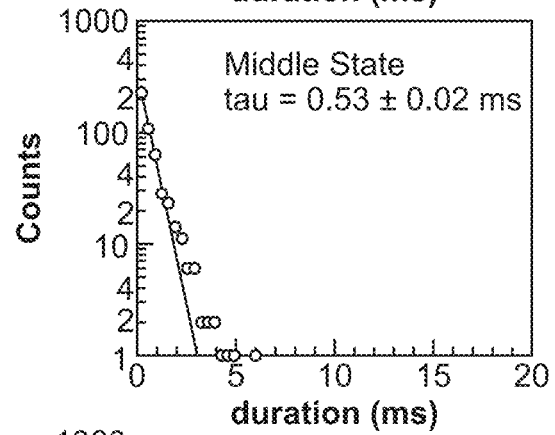
FIG. 18B shows the single-molecule probability distribution function for $I_{med}$, the ATP-bound intermediate complex, during Kemptide processing by a PKA device.
Figure 18C:
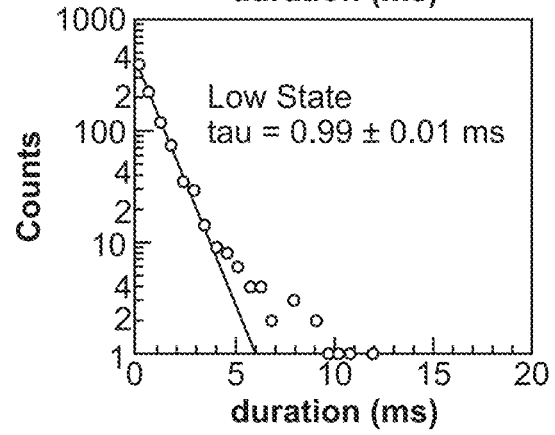
FIG. 18C shows the single-molecule probability distribution function for $I_{Io}$, the fully formed complex during Kemptide processing by a PKA device.

As in the previous embodiments, the complex data allow for statistical analysis of many individual events, in order to determine probability distributions and kinetics of each state and the transitions between them. FIGS. 18A-18C shows histograms of each event of either the $I_{hi}$, $I_{med}$ or $I_{lo}$ state. For each, a fit to the data is provided that gives the mean duration τ of each state. Whereas only two durations ($\tau_{hi}$ and $\tau_{lo}$) exist for a two-state system, three distinct current states provide more parameters from the PKA processivity. Three distinct states exhibit three mean durations and six independent transition probabilities between the states. In addition, binding and unbinding rates can be separately calculated for ATP and Kemptide.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:
1. A single molecule sensing device comprising:
a first electrode;
a second electrode;
a conduction channel connected to the first electrode and the second electrode;
at least one linker molecule having first and second functional groups, the at least one linker molecule having the first functional group non-covalently functionalized with the conduction channel; and
a single sensitizing molecule having a conductivity-modulating component and at least one functional group, said at least one functional group of the single sensitizing molecule being functionalized with the second functional group of the at least one linker molecule, wherein said conductivity-modulating component is within 2 nm of said first functional group non-covalently functionalized with the conduction channel.
2. The single molecule sensing device of claim 1, wherein the conduction channel comprises a single-walled carbon nanotube.
3. The single molecule sensing device of claim 1, wherein the first functional group is a functional group which interacts with the conduction channel through pi-pi stacking.
4. The single molecule sensing device of claim 2, wherein the first functional group is a functional group which interacts with the sidewall of the single-walled carbon nanotube through pi-pi stacking.
5. The single molecule sensing device of claim 1, wherein the single sensitizing molecule having at least one functional group is selected from a group consisting of an enzyme, a protein, a nucleic acid, a ribozyme, an aptamer, and a polysaccharide.
6. The single molecule sensing device of claim 5, wherein the single sensitizing molecule comprises an enzyme selected from a group consisting of lysozyme, protein kinase A, and DNA Polymerase I.
7. The single molecule sensing device of claim 1, wherein the first functional group of the at least one linker molecule is selected from a group consisting of pyrene, benzene, cyclohexane, and 2,3-dichloro-5,6-dicyano-1,4-benzoquinone.
8. The single molecule sensing device of claim 1, wherein the second functional group comprises maleimide.
9. The single molecule sensing device of claim 1, wherein the functional group of the single sensitizing molecule comprises a thiol.
10. The single molecule sensing device of claim 6, wherein the enzyme comprises lysozyme and the first functional group of the at least one linker molecule comprises pyrene.
11. A device for sensing a single molecule, the device comprising:
a first electrode;
a second electrode;
a conduction channel operably coupled to the first and second electrodes; and
a single sensitizing molecule comprising a conductivity-modulating component, said single sensitizing molecule attached to the conduction channel via pyrene maleimide non-covalently attached to the conduction channel, wherein said conductivity-modulating component is within 2 nm of said pyrene maleimide non-covalently attached to the conduction channel.
12. The device of claim 11, wherein the conduction channel comprises a single-walled carbon nanotube.
13. The device of claim 12, wherein the linker molecule interacts with a sidewall of the single-walled carbon nanotube through pi-pi stacking.
14. The device of either of claim 1 or 11, wherein said device is located on a transparent substrate.

* * * * *